US012741085B2

(12) United States Patent
Yang

(10) Patent No.: US 12,741,085 B2
(45) Date of Patent: Sep. 22, 2026

(54) SKIN PATCH DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 597 days.

(21) Appl. No.: 18/269,961

(22) PCT Filed: Sep. 10, 2021

(86) PCT No.: PCT/CN2021/117678
§ 371 (c)(1),
(2) Date: Jun. 28, 2023

(87) PCT Pub. No.: WO2022/148042
PCT Pub. Date: Jul. 14, 2022

(65) Prior Publication Data

US 2024/0066211 A1 Feb. 29, 2024

(30) Foreign Application Priority Data

Jan. 5, 2021 (WO) ................ PCT/CN2021/070207

(51) Int. Cl.
*A61M 5/142* (2006.01)
*A61M 5/145* (2006.01)
(Continued)

(52) U.S. Cl.
CPC .... *A61M 5/14248* (2013.01); *A61M 5/14236* (2013.01); *A61M 5/1452* (2013.01);
(Continued)

(58) Field of Classification Search
CPC .......... A61M 5/14248; A61M 5/14244; A61M 5/1452; A61M 5/172; A61M 99/00;
(Continued)

(56) References Cited

U.S. PATENT DOCUMENTS 3,731,679 A * 5/1973 Wilhelmson ............ F04B 49/06 604/152
4,534,762 A * 8/1985 Heyer .................. A61M 25/02 128/DIG. 26

(Continued)

FOREIGN PATENT DOCUMENTS

CN 206745702 12/2017
CN 109310372 2/2019

(Continued)

OTHER PUBLICATIONS

"International Search Report (Form PCT/ISA/210) of PCT/CN2021/117678," mailed on Nov. 26, 2021, pp. 1-2.

*Primary Examiner* — Nilay J Shah
(74) *Attorney, Agent, or Firm* — JCIP GLOBAL INC.

(57) ABSTRACT

A skin patch drug infusion device includes comprises an infusion mechanism module, a control mechanism module and an adhesive patch. The infusion mechanism module includes an infusion module and a circuit module. The circuit module includes: a circuit board or a three-dimensional circuit coated on the surface of components, for supplying power to specific units; a driving unit, for pushing the driving wheel of the infusion mechanism module to implement drug infusion; a conductive tower-spring, including a middle part with a small diameter and two end parts with a large diameter in the axial direction, for fixing the driving unit and electrically connecting the driving unit and the specific connection end on the circuit board or three-dimensional circuit. The control mechanism module is electrically connected with the infusion mechanism module. The adhesive patch is used for attaching the infusion mechanism module and the control mechanism module to the skin surface.

14 Claims, 12 Drawing Sheets

(51) Int. Cl.

| | |
|---|---|
| ***A61M 5/168*** | (2006.01) |
| ***A61M 5/172*** | (2006.01) |
| ***A61M 99/00*** | (2012.01) |

(52) U.S. Cl.

CPC ........ *A61M 5/1454* (2013.01); *A61M 5/1456* (2013.01); *A61M 5/16831* (2013.01); *A61M 5/172* (2013.01); *A61M 5/1723* (2013.01); *A61M 99/00* (2022.08); *A61M 2005/14208* (2013.01); *A61M 2005/14252* (2013.01); *A61M 2005/14268* (2013.01); *A61M 2005/14506* (2013.01); *A61M 2202/0007* (2013.01); *A61M 2202/04* (2013.01); *A61M 2205/02* (2013.01); *A61M 2205/0216* (2013.01); *A61M 2205/0233* (2013.01); *A61M 2205/0238* (2013.01); *A61M 2205/123* (2013.01); *A61M 2205/18* (2013.01); *A61M 2205/33* (2013.01); *A61M 2205/8206* (2013.01); *A61M 2205/8212* (2013.01); *A61M 2209/088* (2013.01); *A61M 2210/04* (2013.01); *A61M 2230/201* (2013.01)

(58) Field of Classification Search

CPC ............ A61M 5/16831; A61M 5/1723; A61M 2005/14208; A61M 2005/14268; A61M 2205/123; A61M 2205/33; A61B 5/6833; A61B 5/68355

See application file for complete search history.

(56) References Cited

U.S. PATENT DOCUMENTS

| | | | | |
|---|---|---|---|---|
| 4,733,036 | A * | 3/1988 | Koizumi .............. | H01H 13/705 200/276.1 |
| 2007/0219597 | A1* | 9/2007 | Kamen ................. | A61M 5/148 604/404 |
| 2011/0213306 | A1* | 9/2011 | Hanson ............... | A61M 5/1413 604/151 |
| 2016/0367753 | A1 | 12/2016 | Kamen et al. | |
| 2020/0405951 | A1 | 12/2020 | Burren et al. | |

FOREIGN PATENT DOCUMENTS

| | | |
|---|---|---|
| CN | 110691624 | 1/2020 |
| CN | 111939371 | 11/2020 |

* cited by examiner

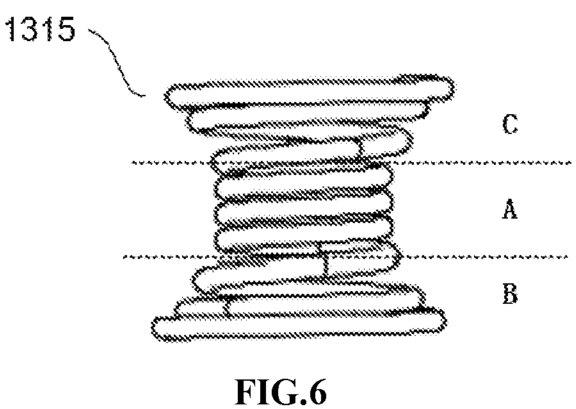
FIG.6
1411
1311
141
1421
142
1316
1316
1317
1314
FIG.7
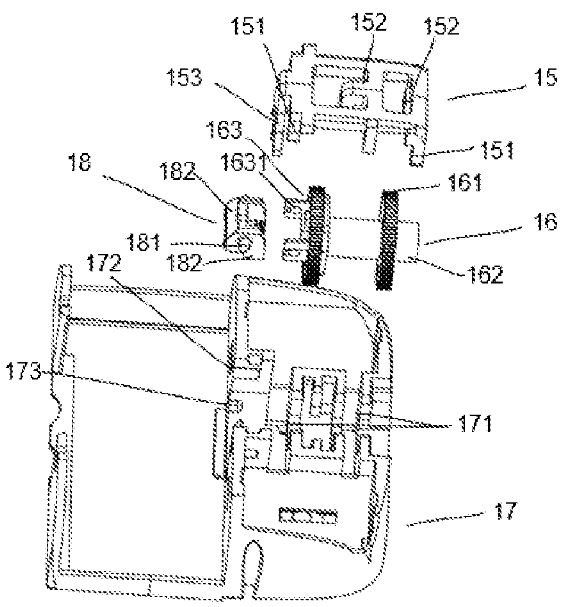
FIG.8a

SKIN PATCH DRUG INFUSION DEVICE

CROSS-REFERENCE TO RELATED APPLICATION

This application is a 371 of international application of PCT application serial no. PCT/CN2021/117678, filed on Sep. 10, 2021, which claims the priority benefit of PCT application no. PCT/CN2021/070207, filed on Jan. 5, 2021. The entirety of each of the above mentioned patent applications is hereby incorporated by reference herein and made a part of this specification.

TECHNICAL FIELD

The present invention mainly relates to the field of medical instruments, in particular to a skin patch drug infusion device and drug filling method.

BACKGROUND

In a healthy person, the pancreas can automatically monitor the amount of glucose in the blood and automatically secrete the required dosage of insulin/glucagon. However, for diabetic patients, the function of their pancreas has been severely compromised, and the pancreas cannot secrete the required dosage of insulin. Therefore, diabetes mellitus is defined as a metabolic disease caused by abnormal pancreatic function, and it is also classified as one of the top three chronic conditions by the WHO. The present medical advancement has not been able to find a cure for diabetes mellitus. Yet, the best the technology could do is control the onset symptoms and complications by stabilizing the blood glucose level for diabetes patients.

Diabetic patients on an insulin pump need to check their blood glucose before infusing insulin into their bodies. At present, most detection methods can continuously detect blood glucose and send the blood glucose data to the remote device in real-time for the user to view. This detection method is called Continuous Glucose Monitoring (CGM), which requires the detection device to be attached to the surface of the patients' skin, and the sensor carried by the device to be inserted into the interstitial fluid for testing. According to the blood glucose (BG) level, the infusion system mimics an artificial pancreas to fill the gaps of the required insulin amount via the closed-loop pathway or the semi-closed-loop pathway.

However, in the present infusion device, the driving unit of the drug infusion device is not stable enough, and it may rotate due to accidental touch, which affects the accuracy of the infusion. At the same time, the reliability of the electrical connection between the driving unit and the circuit board or the specific connection end on the three-dimensional circuit is poor, which affects the infusion effect.

Therefore, in the prior art, there is an urgent need for a drug infusion device with high physic stability and high electrical connection reliability between the driving unit and the specific connection end on the circuit board or the three-dimensional circuit.

BRIEF SUMMARY OF THE INVENTION

The invention discloses a skin patch drug infusion device, the infusion mechanism module is provided with a conductive tower-spring, including a middle part with a small diameter and two end parts with a large diameter in the axial direction, for fixing the driving unit, which can prevent the driving unit from rotating due to accidental touch and affect the accuracy of infusion. At the same time, the conductive tower-spring is electrically connected the driving unit with the specific connection end on the circuit board or three-dimensional circuit, when the conductive tower-spring is compressed, the two ends of the conductive tower-spring are provided with multiple turns of springs to contact with the driving unit and the specific connection end on the circuit board or the three-dimensional circuit, respectively, which can enhance the electrical connection between the conductive tower-spring and the driving unit and the specific connection end on the circuit board or three-dimensional circuit, improving the reliability of the electrical connection.

The invention discloses a skin patch drug infusion device that includes an infusion mechanism module, the infusion mechanism includes an infusion module and a circuit module, the circuit module includes: a circuit board or a three-dimensional circuit coated on the surface of part components, for supplying power to specific units; a driving unit, for pushing the driving wheel of the infusion mechanism module to implement drug infusion; a conductive tower-spring, including a middle part with a small diameter and two end parts with a large diameter in the axial direction, for fixing the driving unit and electrically connecting the driving unit and the specific connection end on the circuit board or three-dimensional circuit; a control mechanism module, electrically connected with the infusion mechanism module; and an adhesive patch, for attaching the infusion mechanism module and the control mechanism module to the skin surface.

According to one aspect of the present invention, the infusion mechanism module further includes a frame, used to carry various components of the infusion mechanism module, the frame is provided with a rotation shaft, the driving unit is sleeved on the rotation shaft and rotated around the rotation shaft.

According to one aspect of the present invention, the diameter of the middle part of the conductive tower-spring remains the same, and the diameter of the two ends gradually expands in a horn-like shape.

According to one aspect of the present invention, the middle part of the conductive tower spring is interference fit with the rotating shaft.

According to one aspect of the present invention, the two ends of the conductive tower-spring are symmetrical.

According to one aspect of the present invention, when the conductive tower-spring is compressed, the two ends of the conductive tower-spring are provided with multiple turns of springs to contact with the driving unit and the specific connection end on the circuit board or the three-dimensional circuit, respectively.

According to one aspect of the present invention, the driving unit includes a driving end, and the number of the driving end is one or two.

According to one aspect of the present invention, the circuit board is a flexible.

According to one aspect of the present invention, the infusion mechanism module further includes a power supply and an elastic conductor with protrusions, used for electrically connecting the power supply and the specific connection end on the circuit board or three-dimensional circuit.

According to one aspect of the present invention, the elastic conductor is one or a combination of a conductive spring, a conductive leaf spring, a conductive rubber, a conductive silica gel.

According to one aspect of the present invention, the power supply is a double-row battery pack.

According to one aspect of the present invention, the infusion mechanism module and the control mechanism module are designed separately, and the control mechanism module can be reused.

According to one aspect of the present invention, the infusion mechanism module and the control mechanism module are disposed of in one housing, discarded together after a single-use.

According to one aspect of the present invention, the control mechanism module is provided with a plurality of first electrical contacts exposed on the surface of the control mechanism module and the infusion mechanism module is provided with a plurality of second electrical contacts electrically connected with the first electrical contacts.

According to one aspect of the present invention, the first electrical contacts or the second electrical contacts is rigid metal pins or elastic conductive members.

According to one aspect of the present invention, the infusion mechanism module further includes a case, the case is provided with an outward extending portion, and a block is provided on the outside of the outward extending portion.

According to one aspect of the present invention, the adhesive patch comprises a tape and a protective film, the first side of the tape is fixedly connected with the infusion device, and the second side opposite the first side of the tape is coated with a paste material. The protective film is fixed around the outer edge of the first side of the tape, the outer edge of the protective film contour is adapted to the outer edge of the tape, and the rockwell hardness of the protective film is higher than the tape.

Compared with the prior art, the technical solution of the present invention has the following advantages:

In the skin patch drug infusion device disclosed by the present invention, the infusion mechanism module is provided with a conductive tower-spring, including a middle part with a small diameter and two end parts with a large diameter in the axial direction, for fixing the driving unit, which can prevent the driving unit from rotating due to accidental touch and affect the accuracy of infusion. At the same time, the conductive tower-spring is electrically connected the driving unit with the specific connection end on the circuit board or three-dimensional circuit, when the conductive tower-spring is compressed, the two ends of the conductive tower-spring are provided with multiple turns of springs to contact with the driving unit and the specific connection end on the circuit board or the three-dimensional circuit, respectively, which can enhance the electrical connection between the conductive tower-spring and the driving unit and the specific connection end on the circuit board or three-dimensional circuit, improving the reliability of the electrical connection.

Furthermore, the diameter of the middle part of the conductive tower-spring remains the same, and it is in interference fit with the rotating shaft to further fix the driving unit and improve the stability of the driving unit.

Furthermore, the two ends of the conductive tower-spring are symmetrically arranged and can be assembled at will to avoid assembly errors.

Furthermore, the infusion mechanism module further includes a power supply and an elastic conductor with protrusions, used for electrically connecting the power supply and the specific connection end on the circuit board or three-dimensional circuit, further improving the reliability of the electrical connection of the infusion mechanism module.

Furthermore, the power supply is double-row battery pack, which can make full use of the internal space and improve the integration of the internal mechanism module in the infusion device.

Furthermore, the circuit board is a flexible circuit board. The flexible circuit board can be flexibly designed according to the internal space of the infusion mechanism module to optimize the internal design of the infusion mechanism module.

Furthermore, the control mechanism module is provided with a plurality of first electrical contacts, the infusion mechanism module is provided with a plurality of corresponding second electrical contacts. The contact area of the electrical connection is small, and it can be designed flexibly, effectively reducing the volume of the control mechanism module and the infusion mechanism module.

BRIEF DESCRIPTION OF THE DRAWINGS

FIG. 6 is a schematic view of the conductive tower-spring according to an embodiment of the present invention.

FIG. 7 is a partially enlarged view of the part M portion in FIG. 4*a* according to en embodiment of the present invention.

FIG. 8*a* and FIG. 8*b* are schematic views of the driving wheel assembly and the frame before and after assembly according to the embodiment of the present application embodiment, respectively.

DETAILED DESCRIPTION

Figure 1A:
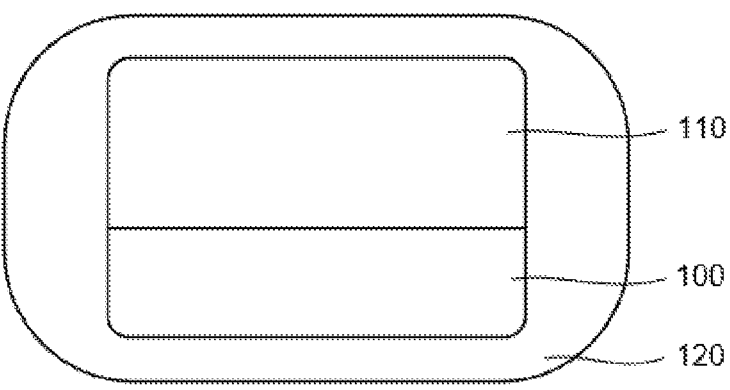
FIG. 1*a* and FIG. 1*b* are schematic top views of the drug infusion device according to two embodiments of the present invention.

As mentioned above, in the prior art, the driving unit of the drug infusion device is not stable enough, and it may rotate due to accidental touch, which affects the accuracy of the infusion. At the same time, the reliability of the electrical connection between the driving unit and the circuit board or the specific connection end on the three-dimensional circuit is poor, which affects the infusion effect.

In order to solve this problem, the present invention provides a drug infusion system. The conductive tower-spring includes a middle part with a small diameter and two end parts with a large diameter, which can enhance the physic stability of the driving unit and electrical connection reliability between the driving unit and the specific connection end on the circuit board or the three-dimensional circuit.

Various exemplary embodiments of the present invention will now be described in detail regarding the figures. The relative arrangement of the components and the steps, numerical expressions and numerical values outlined in the embodiments are not construed as limiting the scope of the invention.

In addition, it should be understood that, for ease of description, the dimensions of the various components shown in the figures are not necessarily drawn in the actual scale relationship; for example, the thickness, width, length or distance of certain units may be exaggerated relative to other mechanism modules.

The following description of the exemplary embodiments is merely illustrative and does not limit the invention its application or use. The techniques, methods, and devices are known to those of ordinary skill in the art and may not be discussed in detail. However, such techniques, methods, and devices should be considered as part of the specification.

It should be noted that similar reference numerals and letters indicate similar items in the following figures. Therefore, once an item is defined or illustrated in a drawing, it will not be discussed further in the following description of the drawings.

Figure 1B:
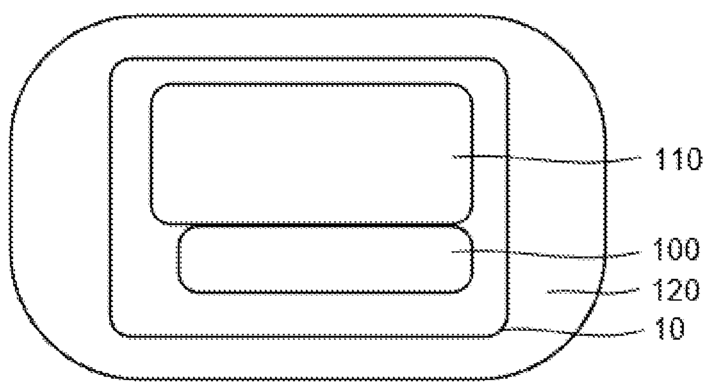

FIG. 1*a* and FIG. 1*b* are schematic top views of the drug infusion device according to two embodiments of the present invention.

In the embodiment of the present invention, the skin patch drug infusion device comprises a control mechanism module 100, an infusion mechanism module 110 and an adhesive patch 120, which will be described separately below. In other embodiments of the present invention, the patch-type drug infusion device may include more parts, which are not specifically limited here.

The patch-type drug infusion device refers to a tubing-free infusion device that is entirely pasted on the user's skin surface by the one piece of adhesive patch 120. And the infusion device is provided with an infusion needle unit 121, integrated on the infusion device, instead of a long tube; therefore, the drug can be directly infused from the drug reservoir 131 to the subcutaneous tissue through the infusion needle unit 121.

In the embodiment of the present invention, the infusion mechanism module 110 and the control mechanism module 100 are designed separately and connected by a waterproof plug or directly engaged and electrically connected into a whole. Details regarding how the reliability of the electrical connection has been improved when the infusion mechanism module 110 and the control mechanism module 100 are directly engaged and electrically connected into a whole will be described below. The control mechanism module 100 can be reused, and the infusion mechanism module 110 is discarded after a single use, as shown in FIG. 1 *a*. In another embodiment of the present invention, the infusion mechanism module 110 and the control mechanism module 100 are connected by a wire and disposed of inside the same housing 10. Attached to a certain position of the user's skin by the adhesive patch 150, both units will be discarded together after a single use, as shown in FIG. 1 *b*.

The patch-type drug infusion device of the embodiment of the present invention includes a control mechanism module 100, which receives signals or information from a remote device or a body fluid parameter detection device (such as CGM), and controls the infusion device to infuse drug(s) accordingly.

Inside the housing 101 of the control mechanism module 100 are disposed of program modules, circuit board(s) and related electronic units for receiving signals or issuing control instructions, as well as other mechanical units or structures necessary for realizing the infusion function, which is not limited herein. In another embodiment of the present invention, a power supply 133 can also be provided in the control structure. Preferably, in the embodiment of the present invention, the power supply 133 is provided in the infusion mechanism module 110, which will be described below.

Figure 2A:
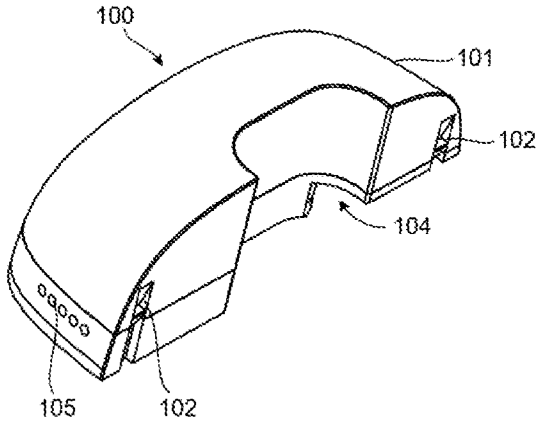
FIG. 2*a* and FIG. 2*b* are schematic views of the control mechanism module according to an embodiment of the present invention.
Figure 2B:
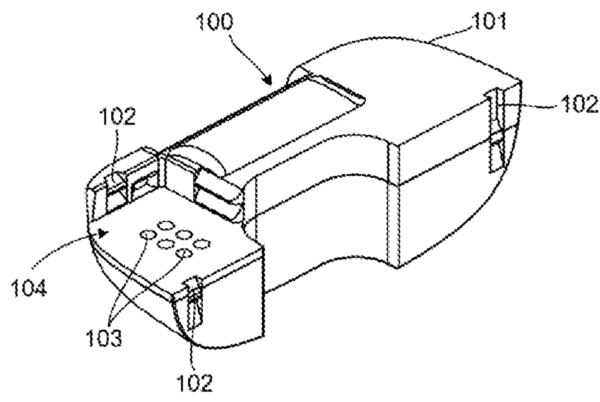

FIG. 2*a* and FIG. 2*b* are schematic views of the control mechanism module according to an embodiment of the present invention.

The control mechanism module 100 further includes the first electrical contact 103 exposed on its surface. The first electrical contact 103 is used as a circuit connection terminal to connect the internal circuits provided in the control mechanism module 100 and the infusion mechanism module 110, respectively. The embodiment of the present invention does not specifically limit the positions of the first electrical contact 103.

Compared with the plug connector used as a connection terminal in the prior arts, the contact area of the electrical contact is much smaller, which provides more flexibility to the mechanism module design, and can effectively reduce the volume of the control mechanism module. At the same time, these smaller electrical contacts can be directly connected to the internal circuit or electrical components. They could also be directly soldered on the circuit board, which helps to optimize the design of the internal circuit and effectively reduce the complexity of the circuit, thereby saving costs and reducing the volume of the infusion system. Furthermore, the electrical contacts are exposed on the surface of the control mechanism module 100 to facilitate electrical connection with connection ends on other mechanism modules.

The type of the first electrical contact 103 includes rigid metal pins or elastic conductive members. Preferably, in the embodiment of the present invention, the first electrical contact 103 is a rigid metal pin. One end of the first electrical contact 103 is electrically connected to the connection end provided inside the control mechanism module 100. In contrast, the other end is exposed on the surface of the lower housing 101*b*. The rest part of the first electrical contact 103 is tightly embedded in the housing 101, thus keeping the internal control mechanism module 100 isolated from the outside.

The elastic conductive member includes conductive spring, conductive silica gel, conductive rubber, or conductive leaf spring. One end of the elastic conductive member is used to electrically connect with the internal connection end in the control mechanism module 100, while the other end is used to connect with other connection ends electrically.

As in an embodiment of the present invention, the first electrical contact 103 is a conductive spring. When the electrical contacts are in contact with each other, the elasticity of the conductive spring can enhance the reliability of the electrical connection. Similar to the rigid metal pin, one end of the conductive spring is exposed on the surface of the lower housing 101*b*. In contrast, the remaining part of the conductive spring is tightly embedded in the housing 101 and electrically connected with internal circuits or electrical components. The connection end disposed inside the control mechanism module 100 can be a conductive lead, a specific part of a circuit, or an electrical element.

It should be noted that the "tightly embedded" in the embodiment of the present invention suggests that there is no gap between the electrical contact and the housing 101, keeping the control mechanism module 100 tightly sealed. The following "tightly embedded" has the same meaning as here.

In another embodiment of the present invention, the first electrical contact 103 is a conductive spring, but it is not tightly embedded in the housing 101. Instead, a sealing element is provided in a groove, both of which are disposed around the area where the first electrical contacts 103 are located, thus sealing the electrical contact area and the control mechanism module 100.

In the embodiment of the present invention, the control mechanism module 100 is further provided with the first engaging portions 102, which is used to fasten the second engaging portion 112 disposed on the infusion mechanism module 110 to assemble the control mechanism module 100 infusion mechanism module 110. Details regarding how the mechanism works to enable the electrical connection between the first electrical contacts 103 and the second electrical contacts 113 (as shown in FIG. 2*a* and FIG. 2*b*) will be described below.

The first engaging portion 102 and the second engaging portion 112 include one or more hooks, blocks, holes, and slots that can be engaged with each other. The positions of the hooks, blocks, holes, and slots can be flexibly adjusted, according to the shape and mechanism module features of the control mechanism module 100 and the infusion mechanism module 110, such as disposed in the interior or on the surface of the corresponding mechanism module, which is not specifically limited herein.

In the embodiment of the present invention, the control mechanism module 100 is further provided with a concave 104 that fits the convex portion 114 disposed at the bottom of the case of the infusion mechanism module 110, which will be described in detail below. Preferably, the first electrical contacts 103 are provided in the concave 104, as shown in FIG. 2*b*.

In the embodiment of the present invention, a buzzer (not shown) is also provided in the control mechanism module 100. When the infusion process starts or ends, the infusion device malfunctions, the drug is exhausted, the control mechanism module 100 issues an error command or receives an error message, etc., the buzzer is used to issue alarm signals, such as sound or vibration, notifying the user to adjust or replace the device in time.

Preferably, in the embodiment of the present invention, the housing 101 of the control mechanism module 100 is provided with a sound-permeable outlet 105 to allow the sound alarm signal from the buzzer to be sent out. In order to achieve a good sealing effect and ensure the normal operation of the buzzer, a waterproof sound-permeable membrane (not shown) is disposed between the sound-permeable outlet 105 and the buzzer. Therefore, the waterproof sound-permeable membrane needs to have a certain porosity to ensure the sound transmission but prevent water molecules penetration.

Compared with the traditional technical solution in which the buzzer is entirely enclosed in the control mechanism module 100, because of the sound-permeable outlet 105, a less loud sound signal emitted from the buzzer would be enough to raise the user's attention, which reduces the energy consumption of the buzzer, thereby optimizing the power consumption configuration of the infusion device and saving production costs.

Figure 3A:
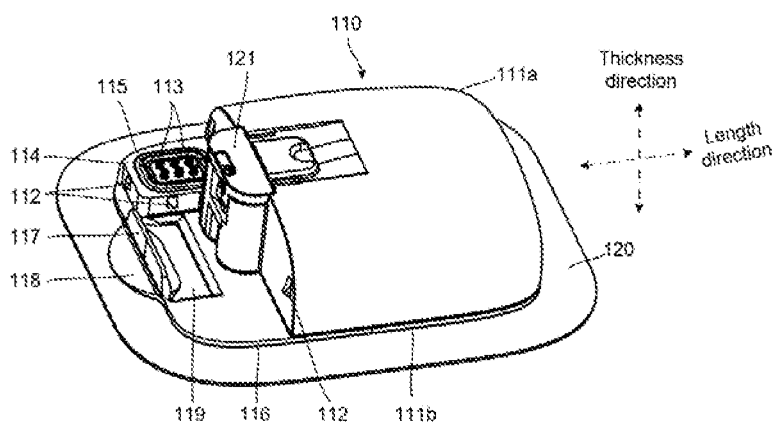
FIG. 3*a* is a schematic view of the infusion mechanism module according to an embodiment of the present invention.
Figure 3B:
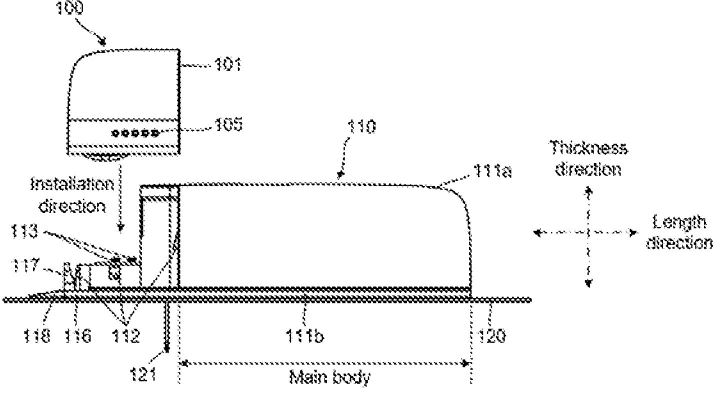
FIG. 3*b* is a side view of the assembly of the control mechanism module and the infusion mechanism module according to an embodiment of the present invention.
Figure 3C:
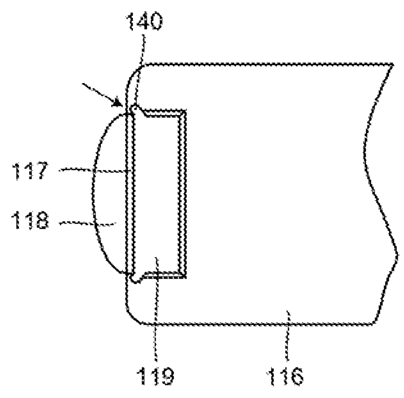
FIG. 3*c* is a schematic top view of the lower case of the infusion mechanism module according to an embodiment of the present invention.
Figure 3D:
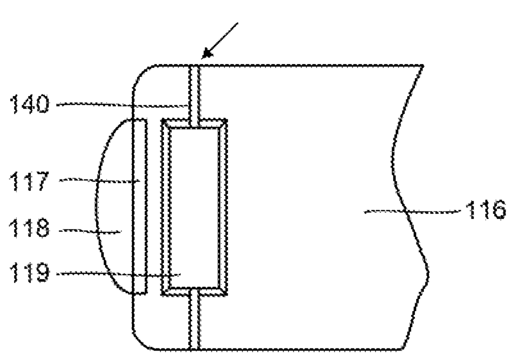
FIG. 3*d* is a schematic top view of the lower case of the infusion mechanism module according to another embodiment of the present invention.

FIG. 3*a* is a schematic view of the infusion mechanism module 110 according to the embodiment of the present invention. FIG. 3*b* is a side view of the assembly of the control mechanism module 100 and the infusion mechanism module 110 according to the embodiment of the present invention. FIG. 3*c* is a schematic top view of the lower case of the infusion mechanism module according to an embodiment of the present invention. FIG. 3*d* is a schematic top view of the lower case of the infusion mechanism module according to another embodiment of the present invention.

The skin patch drug infusion device further includes an infusion mechanism module 110 with a case. A mechanical module, an electric control module, and other auxiliary modules for completing the drug infusion process are provided inside the case, which will be described in detail below. The case of the infusion mechanism module 110 may include multiple parts. As in the embodiment of the present invention, the case of the infusion system includes an upper case 111*a* and a lower case 111*b*.

As mentioned above, in the embodiment of the present invention, the infusion mechanism module 110 is provided with the second engaging portions 112, which is used to engaged and fasten the corresponding first engaging portions 102. The positions where the first engaging portions 102 and the second engaging portions 112 are provided correspondingly.

In the embodiment of the present invention, the infusion mechanism module 110 is provided with second electrical contacts 113, which are used to press against the corresponding first electrical contacts 103 to create an electrical connection between the control mechanism module 100 and the infusion mechanism module 110. The compression between these two corresponding electrical contacts disposed on different structures can improve the reliability of the electrical connection. Similar to the first electrical contacts 103, one of the second electrical contact 113 also includes a rigid metal pin and an elastic conductive member. Preferably, in the embodiment of the present invention, the second electrical contact 113 is a conductive spring. Similarly, the conductive spring can improve the electrical connection performance. A groove is also arranged around the area where the second electrical contact 113 is disposed, and a sealing member 115 is arranged in the groove. Similarly, the elasticity of the conductive spring can further improve the electrical connection performance.

Preferably, in the embodiment of the present invention, the two ends of the conductive spring have different diameters. And the diameter of the end exposed to the outside of the infusion mechanism module 110 is shorter than that of the end inside the infusion mechanism module 110. In this way, the conductive spring can be held in the case because of the longer diameter; Thus, when the control mechanism module 100 is not installed on the infusion mechanism module 110, the longer diameter of the inner end can prevent the conductive spring from detaching from the infusion mechanism module 110.

The embodiment of the present invention does not limit the position at where second electrical contacts 113 are arranged, as long as it can be electrically connected to the corresponding first electrical contacts 103. Preferably, in the embodiment of the present invention, the upper case 111*a* of the infusion mechanism module 110 includes a convex portion 114 where the second electrical contacts 113 are disposed, as shown in FIG. 3*a*. The shape of the convex portion 114 corresponds to that of the concave 104 disposed on the control mechanism module 100, allowing the two portions to tightly fit each other and press the first electrical contacts 103 and the corresponding second electrical contacts 113 against each other to realize the electrical connection.

In other embodiments of the present invention, the convex portion 114 may be provided on the lower case 111*b*. When the infusion mechanism module 110 includes an integral case, the convex portion 114 will be a part of the integral case not specifically limited herein.

The method of assembling the control mechanism module 100 and the infusion mechanism module 110 to each other includes pressing the control mechanism module 100 on the infusion mechanism module 110 along the thickness direction of the infusion mechanism module 110, thereby engaging the first engaging portion 102 and the second engaging portion 112; or pressing the control mechanism module 100 on the infusion mechanism module 110 along the length direction of the infusion mechanism module 110. Alternatively, the control mechanism module 100 can be pressed along with any angle between the thickness direction and the length direction of the infusion mechanism module 110, making the first engaging portion 102 and the second engaging portion 112 engaged with each other. Preferably, in the implementation of the present invention, the method by which the control mechanism module 100 and the infusion mechanism module 110 are assembled is to press the control mechanism module 100 on the infusion mechanism module 110 along with the thickness direction of the infusion mechanism module 110, making the first engaging portion 102 and the second engaging portion 112 engaged with each other, as shown the installation direction in FIG. 3*b*.

In the embodiment of the present invention, the lower case 111*b* of the infusion mechanism module 110 further includes an outward extending portion 116. A block 117 is provided outside the outer extending portion 116, as shown in FIG. 3*a*. As mentioned above, the control mechanism module 100 is pressed to the engaging position along the thickness direction of the infusion mechanism module 110; thus, block 117 can prevent the control mechanism module 100 from detaching along the length direction of the infusion mechanism module 110, ensuring the normal operation of the infusion system. Obviously, in another embodiment of the present invention, if the control mechanism module 100 is pressed to the engaging position along with other directions, the control mechanism module 100 can also be prevented from detaching from the infusion mechanism module 110 by adjusting the position of the block 117.

It should be noted here that “outer” and “outside” are relative to the main body of the infusion mechanism module 110, where they belong to a concept of the relative position, as shown in FIG. 3*a* or FIG. 3*b*. The “outside” below have the same meaning as here.

In the embodiment of the present invention, the outer end of the outer extending portion 116 is also provided with a pressing portion 118 for releasing the blocking effect of block 117. While the user is replacing the infusion mechanism module 110, the control mechanism module 100 can be released from block 117 by pressing the pressing portion 118 with a finger. Then, the user can remove the control mechanism module 100 from the infusion mechanism module 110 with two fingers.

Another embodiment of the present invention can also be provided with an unlocking hole 119 disposed of in the inner side of block 117. While the pressing portion 118 is pressed, a finger can enter the unlocking hole 119, thereby pushing the control mechanism module 100 out to separate the control mechanism module 100 from the infusion mechanism module 110. In the embodiment of the present invention, the unlocking hole 119 is square. The square unlocking hole 119 can facilitate the smooth entry of fingers. In other embodiments of the present invention, the unlocking hole 119 may also have other shapes, which is not specifically limited here.

The lower case 111*b* of the infusion mechanism module 110 is also provided with one or more crease grooves 140. Two crease grooves 140 are provided on both sides of the unlocking hole 119, as shown in FIG. 3*c* and FIG. 3*d*. After the crease groove, 140 is provided, the thickness or width of the lower case 111*b* at the crease groove 140 (as shown by the arrows in FIG. 3*c* and FIG. 3*d*) is reduced. When the user presses the pressing portion 118, the lower case 111*b* is easily broken at the crease groove 140, and the blocking of the control mechanism module 100 by block 117 is more smoothly released.

Preferably, in the embodiment of the present invention, two crease grooves 140 are provided at the both ends of block 117, respectively, as shown in FIG. 3*c*. In another embodiment of the present invention, the crease groove 140 is provided on two corresponding lateral sides of the unlocking hole 119, as shown in FIG. 3*d*.

The skin patch drug infusion device further includes a needle unit 121, used for infusing the drug to the subcutaneous tissue.

An adhesive patch 120 is also provided on the bottom of the lower case 111*b* to attach the infusion device to the user's skin surface.

Figure 4A:
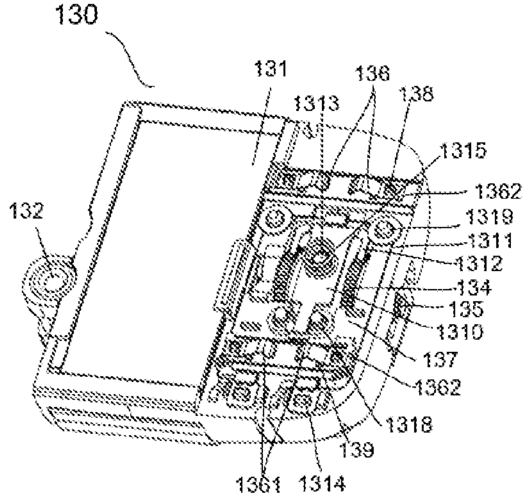
FIG. 4*a* and FIG. 4*b* are schematic views of the internal mechanism module of the infusion mechanism module according to an embodiment of the present invention, respectively.
Figure 4B:
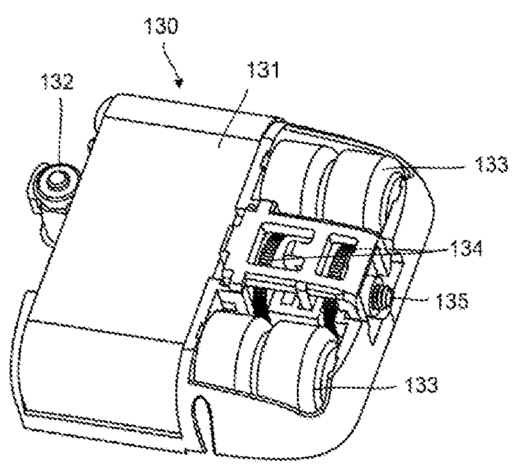
Figure 4C:
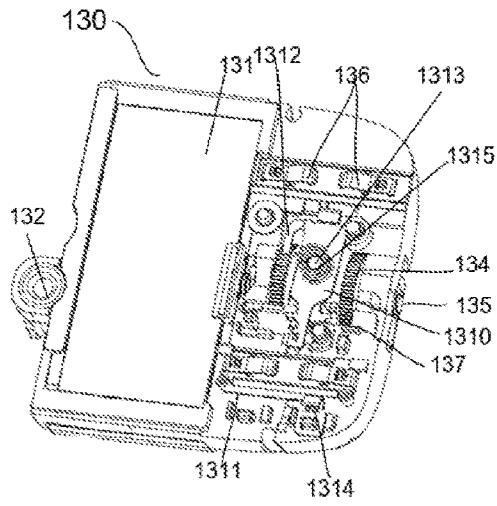
FIG. 4*c* is a schematic view of the internal mechanism module of the infusion mechanism module according to another embodiment of the present invention.

FIG. 4*a* and FIG. 4*b* are two schematic views of the internal mechanism module 130 of the infusion mechanism module 110 of the embodiment of the present invention from two perspectives, respectively. FIG. 4*c* is a schematic view of the internal mechanism module 130 of the infusion mechanism module according to another embodiment of the present invention.

Figure 14:
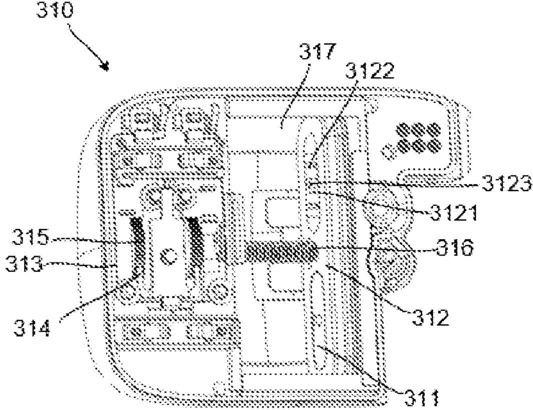
FIG. 14 is a schematic view of the infusion mechanism module's internal mechanism module comprising a blockage detection module according to another embodiment of the present invention.

In the embodiment of the present invention, the internal mechanism module 130 includes mechanical units and electronic control units used to realize the infusion function, such as a drug reservoir 131, a drug outlet 132, a power supply 133, a driving wheel 134, a screw 135, a circuit board (not shown), a driving unit 1310, etc. The movement of the driving unit 1310 drives the driving wheel 134 to rotate, thus making the screw 135 push the piston 312 (as shown in FIG. 14) in the drug reservoir 131 forward, realizing the drug infusion.

In the embodiment of the present invention, the power supply 133 is a conventional button battery. In other embodiments of the present invention, the power supply 133 may also be other types of batteries, as long as it can meet the requirements for supplying power to the infusion system. Preferably, in the embodiment of this present invention, the type of the power supply 133 is a double-row battery pack; that is, two rows of button batteries are arranged on both sides of the driving wheel 134, respectively, as shown in FIG. 4*b*. Conventionally, the discharge capacity of button batteries is low. The double-row button battery pack can reduce the discharge level of each battery, thereby extending the service life of the battery. Furthermore, the double-row design of the power supply 133 can make the full use of the internal space and improve the integration within the internal mechanism module in the infusion system.

The infusion mechanism module 110 in the embodiment of the present invention is also provided with a circuit board or multiple three-dimensional circuits coated on the surface of a part of the mechanism module for supplying power to specific structural units. According to the internal arrangement characteristics of the infusion device, the shape and position of the three-dimensional circuit can be flexibly designed, which can make the full use of the internal space of the infusion mechanism module, making the arrangement more compact. The circuit board is a hard/rigid circuit board or a flexible circuit board. Preferably, in the embodiment of the present invention, the circuit board is flexible. The shape of the flexible circuit board is adjustable, allowing it to be flexibly designed according to the internal space of the infusion mechanism module 110. At the same time, multiple connection ends can be provided on the flexible circuit board to be electrically connected to second electrical contacts 113, thereby connecting the circuits of the control mechanism module 100 and the infusion mechanism module 110, allowing the infusion system to perform drug infusion function.

An elastic conductor 136 is also provided inside the infusion mechanism module 130. The elastic conductor 136 is electrically connected to the power supply 133, and the specific connection end on the circuit board (or three-dimensional circuit), thereby supplying power to specific structural units.

Figure 5:
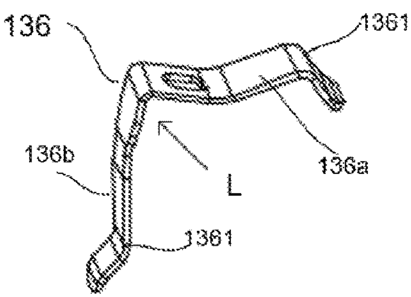
FIG. 5 is a schematic view of the elastic conductor according to an embodiment of the present invention.

FIG. 5 is a schematic view of the elastic conductor according to an embodiment of the present invention.

In the embodiment of the present invention, the elastic conductor 136 includes a first elastic conductor 136*a* and a second elastic conductor 136*b*, the first elastic conductor 136*a* is connected with the power supply 133, and the second elastic conductor 136*b* is connected with the specific connection end on the circuit board (or three-dimensional circuit). At least a protrusion 1361 is provided on the first elastic conductor 136*a* and the second elastic conductor 136*b*, which facilitate the point contact connection or the line contact connection between the first elastic conductor 136*a* and the power supply 133, and also facilitate the point contact connection or the line contact connection between the second elastic conductor 136*b* and the specific connection end on the circuit board (or three-dimensional circuit), thereby improving the electrical connection reliability between the elastic conductor 136 and the power supply 133, and the specific connection end on the circuit board (or three-dimensional circuit). When the first elastic conductor 136*a* and the second elastic conductor 136*b* is flat, during use, it is likely to cause a poor connection between the elastic conductor 136 and the power supply 133 and the specific connection end on the circuit board (or three-dimensional circuit), thereby affecting the use effect. In the embodiment of the present invention, protrusion 1361 may be a linear protrusion formed by bending the first elastic conductor 136*a* or the second elastic conductor 136*b*, or it may be several dots or other shapes of protrusions formed by other means on the first elastic conductor 136*a* or the second elastic conductor 136*b*. The form and number of the protrusions 1361 on the first elastic conductor 136*a* or the second elastic conductor 136*b* can be the same or different. Here, the form, number, and forming method of the protrusions 1361 are not specifically limited, as long as the point contact connection or line contact connection between the elastic conductor 136 and the power supply 133 and the specific connection end on the circuit board (or three-dimensional circuit) can be enhanced, improving the reliability of the electrical connection.

In the embodiment of the present invention, the first elastic conductor 136*a* and the second elastic conductor 136*b* are approximately arranged in an "L" shape, the first elastic conductor 136*a* is approximately parallel to the frame 137, and the second elastic conductor 136*b* is approximately perpendicular to the frame 137. In other embodiments of the present invention, the first elastic conductor 136*a* and the second elastic conductor 136*b* can also be arranged in other shapes, which are not specifically limited here, as long as the power supply 133 and the specific connection end on the circuit board (or three-dimensional circuit) can be electrically connected. An insulating member 1362 is also provided at the junction of the first elastic conductor 136*a* and the second elastic conductor 136*b* (as shown at the position L in FIG. 4*c*) to prevent the power unit 1311 from contacting the elastic conductor 136 and causing a short circuit during operation, further stop the infusion mechanism module 130 from working. In the embodiment of the present invention, the insulating member 1362 is formed by printing ink. In other embodiments of the present invention, the insulating member 1362 may also be insulating glue, insulating varnish or insulating material, which is not specifically limited herein.

In the embodiment of the present invention, the elastic conductor 136 may be a sheet metal including the first elastic conductor 136*a* and the second elastic conductor 136*b* or may be intergrated by the single first elastic conductor 136*a* and the single second elastic conductor 136*b* which are directly electrically connected or indirectly electrically connected with other conductive elements, which is not limited herein. When the elastic conductor 136 is a sheet metal including the first elastic conductor 136*a* and the second elastic conductor 136*b*, which not only make the elastic conductor 136 with simple technological process, firm connection between the elastic conductor 136*a* and the second elastic conductor 136*b*, but also reduce the volume of the elastic conductor 136, save the material and the the raw material and technological cost. When the elastic conductor 136 is intergrated by directly electrically connecting the first elastic conductor 136*a* and the second elastic conductor 136*b* or indirectly electrically connected with other conductive elements, the elastic member can be flexibly selected according to the requirements of the specific connecting components to optimize the internal design of the infusion mechanism module.

In the embodiment of the present invention, the frame 137 is further provided with a positioning post 138, the elastic conductor 136 is provided with an opening corresponding to the positioning post 138, and the elastic conductor 136 is sleeved on the positioning post 138 through the opening, so that the elastic conductor 136 is fixed to the frame 137. At the same time, the positioning post 138 is melted by hot melting to further fixed the elastic conductor 136 and to prevent the elastic conductor 136 from shaking due to long-term use or other reasons, which cause the poor electric connection between the elastic conductor 136 and the power supply 133 and the specific connection end on the circuit board (or three-dimensional circuit) and affect the use.

In the embodiment of the present invention, a boss 139 is also provided on frame 137. The boss 139 is located below the first elastic conductor 136*a* to prevent the protrusion 1361 of the first elastic conductor 136*a* from being flattened or deformed during long-term use, which results in a poor electrical connection between the first elastic conductor 136*a* and the specific connection end on the circuit board (or three-dimensional circuit), causing a malfunction. Preferably, the setting position of the boss 139 deviates from the projection position of the protrusion 1361 on the frame 137 and is close to the position post 138. On the one hand, it can prevent the circuit board from being damaged by hard contact or compression between the first elastic conductor 136*a* and the specific connection end on the circuit board (or three-dimensional circuit). On the other hand, it can ensure the elastic electrical contact between the first elastic conductor 136*a* and the specific connection end on the circuit board (or three-dimensional circuit).

Similar to the elastic conductive member above mentioned, the type of the elastic conductor 136 includes a conductive spring, a conductive leaf spring, a conductive rubber, a conductive silica gel, etc., which are not specifically limited herein, as long as they can meet the requirements for electrically connecting the power supply 133 to specific connection ends on the circuit board (or three-dimensional circuit). Preferably, in the embodiment of the present invention, the elastic conductor 136 is the conductive leaf spring. Since the infusion mechanism module 110 has a double-row battery pack, the multiple conductive leaf springs are also designed as a double-row pack, as shown in FIG. 4*a*.

As shown in FIG. 4*a*, the interior of the infusion mechanism module 110 also includes a drive unit 1310 and a power unit 1311, arranged on the frame 137. Frame 137 is also provided with a rotation shaft 1313, the drive unit 1310 is provided with a through hole, and the drive unit 1310 is sleeved on the rotation shaft 1313 through a through hole for fixing. The elastic conductor 136 can realize a direct electrical connection between the power supply 133 and the specific structural units, which helps to optimize the internal circuit design and reduce the complexity of the internal mechanism module. The driving unit 1310 includes a driving end 1312. One end of the power unit 1311 is connected to the driving unit 1310, and the other end is connected to a specific connection ends on the circuit board or three-dimensional circuit through the conductive platform 1314 so as to further realize the connection with the control module in the control mechanism module 100. The control module in the control mechanism module 100 applies power to the power unit 1311, the drive unit 1310 rotates around the rotation shaft 1313, drives the drive end 1312 forward to push the gear teeth of the drive wheel 134 forward, and causes the infusion device to perform drug delivery. In the embodiment of the present invention, there are two driving ends 1312 and two corresponding power units 1311. In another embodiment of the present invention, there is one driving end 1312 and one power unit 1311, as shown in FIG. 4*c*.

The infusion mechanism module 110 is also provided with a conductive tower-spring 1315 sleeved on the rotating shaft 1313, with one end abuts the drive unit 1310, and the other end electrically connected to a specific connection end on the circuit board or three-dimensional circuit for fixing the drive unit 1310, at the same time, realize the electrical connection between the driving unit 1310 and specific connection ends on the circuit board or three-dimensional circuit.

FIG. 6 is a schematic view of the conductive tower-spring according to an embodiment of the present invention.

In the embodiment of the present invention, the conductive tower spring 1315 includes a part A with a small diameter at the central part in the axial direction and a part B and a part C with a large diameter at both ends. The diameter of part A remains the same, and the rotation shaft 1313 is fixed by interference fit, further, fix the drive unit 1310, and at the same time, part B abuts the drive unit 1310 to prevent the drive unit 1310 from shaking due to instability when it is accidentally touched, causing the drive end 1312 to push the drive wheel 134 forward, which affects the accuracy of the infusion. The diameter of the B part and the C part gradually expand towards the two ends in a horn-like shape. When the B part and the C part are respectively electrically connected to the drive unit 1310 and the specific connection ends on the circuit board or three-dimensional circuit, the conductive tower-spring 1315 is compressed; therefore, part B and part C have multiple turns, and at least 2-3 turns of springs are in contact with the driving unit 1310 and the specific connection ends on the circuit board or three-dimensional circuit at the same time, thereby improving the electrical connection reliability of the infusion device. Preferably, in the embodiment of the present invention, parts B and C of the conductive tower-spring 1315 are symmetrical, and the two ends can be assembled at will to avoid assembly misalignment.

FIG. 7 is a partially enlarged view of the part M portion in FIG. 4*a* according to the embodiment of the present invention.

In the embodiment of the present invention, at least one conductive platform 1314 is provided inside the infusion mechanism module 110. Specifically, when the driving unit 1310 includes two driving arms 1312, there are two corresponding power units 1311 and conductive platforms 1314, as shown in FIG. 4*a*. When the driving unit 1310 includes one driving arm 1312, there is one corresponding power unit 1311 and one conductive platform 1314, as shown in FIG. 4*c*. The conductive platform 1314 is electrically connected to the power unit 1311 and the specific terminal on the circuit board or three-dimensional circuit, respectively.

The conductive platform 1314 includes a conductive platform body 141 and a conductive arm 142. The conductive arm 142 is an elastic conductive element. At least one conductive platform protrusion 1421 is provided on the conductive arm 142 to facilitate the connection with specific connection ends on the circuit board (or three-dimensional circuit), improving the electrical connection reliability of the conductive platform 1314 and the specific connection ends on the circuit board (or three-dimensional circuit). When the conductive arm 142 of the conductive platform 1314 is flat, it is likely to cause the poor connection between the conductive platform 1314 and specific connection ends on the circuit board (or three-dimensional circuit) during use, thereby affecting the use effect. In the embodiment of the present invention, conductive platform protrusion 1421 may be a linear protrusion formed by bending conductive arm 142, or it may be several dots or other shapes of protrusions formed by other means on conductive arm 142. Here, the form, number, and forming method of conductive platform protrusion 1421 are not specifically limited, as long as the point contact connection or line contact connection between the conductive platform 1314 and the specific connection ends on the circuit board (or three-dimensional circuit) can be enhanced, improving the reliability of the electrical connection. In the embodiment of the present invention, the conductive platform body 141 further includes an end portion 1411 of the conductive platform body, and the power unit 1311 is an electric drive type linear driver or an electric heating type linear driver, such as a shape memory alloy, which is connected to the conductive platform body 141 by die casting, causing stable connection and highly reliable electrical connection. Specifically, the power unit 1311 is put into the end portion 1411 of the conductive platform body after being folded in half and then connected to the end portion 1411 of the conductive platform body 141 by die-casting method further improving the reliability of the electrical connection.

In the embodiment of the present invention, the conductive platform 1314 may be a sheet metal including the conductive platform body 141 and conductive arm 142, or may be formed by the single conductive platform body 141 and the single conductive arm 142 directly electrically connected or indirectly electrically connected with other conductive elements, which is not limited herein. When the conductive platform 1314 is a sheet metal including the conductive platform body 141 and the conductive arm 142, which not only make the conductive platform 1314 with simple technological process, firm connection between the conductive platform body 141 and conductive arm 142, but also reduce the volume of the conductive platform 1314, save the material and the the raw material and technological cost. When the conductive platform 1314 is integrated by the single conductive platform body 141 and the single conductive arm 142 directly electrically connected or indirectly connected with other conductive elements, the conductive member can be flexibly selected according to the requirements of the specific connecting components to optimize the internal design of the infusion mechanism module.

Similarly, the conductive platform body 141 and the conductive platform body end portion 1411 can also be sheet metal or integrated by directly or indirectly electrically connecting with other conductive elements, which is not limited herein. The conductive platform 1314 is a sheet metal including the conductive platform body 141, the conductive arm 142 and the conductive platform body end portion 1411, or the two of them can be a sheet metal and then integrated with the third party directly or indirectly through other conductive elements, or all of the three parts are directly integrated or indirectly integrated by electrical connection with other conductive elements, and there is no specific limitation here. The benefits of various forming methods are described above, so it will not be repeated here. Preferably, in the embodiment of the present invention, the conductive platform body 141, the conductive arm 142 and the conductive platform body end portion 1411 are integrally formed.

In the embodiment of the present invention, a plurality of stoppers 1316 are provided on the frame 137 for accommodating and limiting the position of the conductive platform 1314, the frame 137 is further provided with a conductive platform positioning post 1317, the conductive platform 1314 is provided with an opening corresponding to the conductive platform positioning post 1317, and the conductive platform 1314 is sleeved on the conductive platform positioning post 1317 through the opening, so that the conductive platform 1314 is fixed to the frame 137. At the same time, the conductive platform positioning post 1317 is melted by hot melting to further fixed the conductive platform 1314 and to prevent the conductive platform 1314 from shaking due to long-term use or other reasons, which cause the poor electric connection between the conductive platform 1314 and the power supply 133 and the specific connection end on the circuit board (or three-dimensional circuit) and affect the use.

In the embodiment of the present invention, a conductive platform boss (not shown) is also provided on the frame 137, and the conductive platform boss is located below the conductive arm 142 to prevent the conductive platform protrusion 1421 of the conductive arm 142 from being flattened or deformed during long-term use, which results in a poor electrical connection between the conductive arm 142 and the specific connection end on the circuit board (or three-dimensional circuit), causing a malfunction. Preferably, the setting position of the conductive platform boss deviates from the projection position of the conductive platform protrusion 1421 on the frame 137 and it is close to the conductive platform positioning post 1317. On the one hand, it can prevent the circuit board from being damaged by hard contact or compression between the conductive arm 142 and the specific connection end on the circuit board (or three-dimensional circuit). On the other hand, it can ensure the elastic electrical contact between the conductive arm 142 and the specific connection end on the circuit board (or three-dimensional circuit).

Similar to the elastic conductor 136 above mentioned, the type of the conductive platform 1314 includes a conductive spring, a conductive leaf spring, a conductive rubber, a conductive silica gel, etc., which are not specifically limited herein, as long as they can meet the requirements for electrically connecting the driving unit 1310 to specific connection ends on the circuit board (or three-dimensional circuit).

Figure 8B:
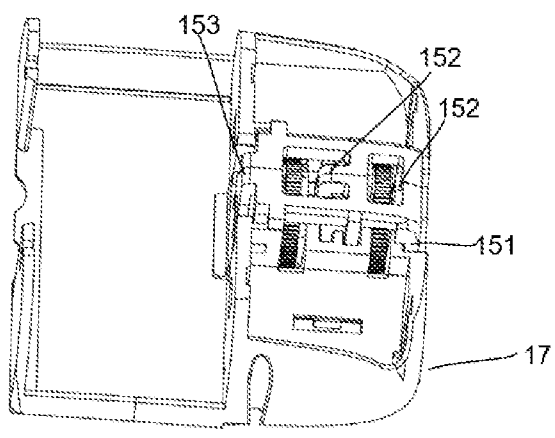
Figure 8C:
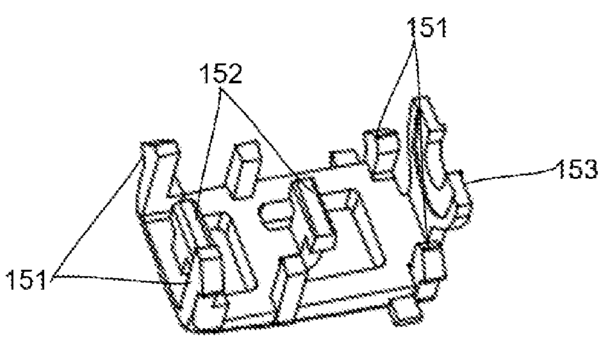
FIG. 8*c* is a schematic view of the shield according to an embodiment of the present invention.

FIG. 8*a* and FIG. 8*b* are schematic views of the driving wheel assembly and the frame before and after assembly according to the embodiment of the present application embodiment, respectively. FIG. 8*c* is a schematic view of the shield according to an embodiment of the present invention.

The driving wheel assembly includes a driving wheel body 16 and a movable block 18. The driving wheel body 16 includes a driving wheel 161, a driving tube 162, which is provided with threads for accommodating the screw 135, and a connecting piece 163 arranged at the end of the driving wheel 161. The connecting piece 163 is provided with a connecting portion 1631, operatively connected with the movable block 18. The movable block 18 is provided with threads to accommodate the screw 135. The movable block 18 is also provided with a movable block connecting rod 181, which is mobily connected with the connecting portion 1631. After the connecting rod 181 is mobily connected with the connecting portion 1631, the movable block 18 can rotate around the connecting rod 181 to open or close the movable block 18. When the movable block 18 is opened, the screw 135 can slide to the driving wheel body 16, and when the movable block 18 is closed, the screw 135 cannot slide to the driving wheel body 16, which will be described in detail below.

The driving wheel assembly further includes a shield 15, and a plurality of shield engaging portions 151 are provided on the shield 15 for engaging with the frame 17. The frame 17 is provided with a frame groove 171 for accommodating the driving wheel body 16 and a plurality of frame engaging portions 172 for engaging with the shield engaging portions 151. After the driving wheel body 16 and the movable block 18 are connected and put into the frame groove 171, the shield 15 is assembled to the frame 17. By the engagement of the frame engaging portion 173 and the shield engaging portion 151, the driving wheel body 16 and the movable block 18 are fixed in the frame 17 to prevent the shaking of the driving wheel assembly and affect the accuracy of drug infusion.

The frame engaging portions 173 and the shield engaging portion 151 include hooks, blocks, holes, and grooves that can be engaged with each other. The position of the engaging portions can be flexibly designed according to the shape and design of the frame 17 and the shield 15, and is not specifically limited here. Preferably, the space formed by the plurality of frame engaging portions 173 and the plurality of shield engaging portions 151 can accommodate the driving wheel body 16 and the movable block 18 to prevent the driving wheel body 16 from shaking.

In the embodiment of the present invention, the shield 15 is also provided with at least one elastic arm 152 for elastically abutting the drive tube 162, which can further fix the drive wheel body 16, improving the stability of the infusion mechanism module 110 and the accuracy of drug infusion. Preferably, two elastic arms 152 are arranged on both sides of one of the driving wheels 161 and abut against the driving tube 162, respectively. As shown in FIG. 8*b*, the driving wheel body 16 is fixed at multiple points.

The shield 15 is also provided with a baffle 153, and the baffle 153 is provided with a mouth. The main frame 17 is also provided with a card slot 173 on the side close to the reservoir 131 for accommodating the strip (not shown). The strip abuts against the baffle 153 to form a through hole for accommodating the screw 135 and at the same time confine the driving wheel body 16 and the movable block 18 in the frame 17. Preferably, the mouth of the baffle 153 is semi-circular, and the diameter is adapted to the diameter of the screw 135, so as to better accommodate the screw 135 and prevent the screw 135 from shaking greatly under the action of external force.

Preferably, in the embodiment of the present invention, the shield 15 is integrally molded; the technological process is simple, the the volume is small, the connection is firm, the material is saved, and the cost is reduced.

FIG. 9*a*-FIG. 9*d* are schematic views of the movable block opened or closed according to an embodiment of the present invention, respectively.

The movable block 18 further includes an upper movable block 182 and a lower movable block 183, and the lower movable block 183 is also provided with a lower movable block end 1831. The movable block 18 opened means that the upper movable block 182 is close to the driving wheel 161, and the lower movable block 183 is far away from the driving wheel 161. The thread in the movable block 18 does not engage with the screw 135. The screw 135 can be smoothly slid in the movable block 18 and the driving tube 162. The movable block 18 closed means that the upper movable block 182 is far away from the driving wheel 161, and the lower movable block 183 is close to the driving wheel 161. At this time, the thread in the movable block 18 is engaged with the screw rod 135, and the screw 135 cannot slide in the movable block 18 and the driving tube 162.

In the embodiment of the present invention, an arc-shaped blocking member 174 is also provided on the frame 17 to limit the position of the lower movable block 183. When the movable block 18 is opened, that is, the upper movable block 182 is close to the driving wheel 161 and the lower movable block 183 is far away from the driving wheel 161, the lower movable block end 1831 of the lower movable block 183 is located outside the arc-shaped blocking member 174, so that the movable block 183 is kept open. At this time, the thread in the movable block 18 does not engage with the screw 135, and the screw 135 can slide smoothly in the movable block 18 and the drive tube 162. When the movable block 18 is opened, the reservoir 131 can be filled with the drug. In the filling process to the reservoir 131, the screw 135 can smoothly move to the end of the driving wheel 161 under the pushing action generated during the filling process, until the filling is completed, no need for the assistance of other parts, which can simplify the complexity of the infusion mechanism module, improve the integration level, save cost, and reduce the volume of the infusion mechanism 110, and at the same time maximizing the actual storage volume of reservoir 131.

When the movable block 18 is closed, that is, the movable block 182 is far away from the driving wheel 161 and the lower movable block 183 is close to the driving wheel 161, the lower movable block end 1831 of the lower movable block 183 is located inside the arc-shaped blocking member 174, and the movable block 18 is kept closed. At this time, the thread in the movable block 18 is engaged with the screw 135, and the screw 135 cannot slide in the movable block 18 and the drive tube 162. When the infusion device 110 performs the drug infusion after the drug is filled, the driving end 1312 of the driving unit 1310 pushes the driving wheel 161 forward, and the movable block 18 rotates with the driving wheel 161. During the rotation, after the lower movable block end 1831 bypasses the arc-shaped blocking member 174, since there is no resistance from the arc-shaped blocking member 174, the lower movable block end 1831 falls into the inside of the arc-shaped blocking member 174. At the same time, since the movable block 18 is kept closed, the screw 135 can only move away from the driving wheel 161 under the pushing action of the rotation of the driving wheel 161 and perform the drug infusion. There is no need to worry about the free movement of the screw 135 due to the engagement failure of the screw 135 with the movable block 18 or the drive tube 162, which will affect the infusion effect or even cause the infusion device to disable.

In the embodiment of the present invention, a notch 1611 is provided on the end face of the driving wheel 16, close to the reservoir 131, the shape is adapted to the lower movable block 183, and is used for accommodating the lower movable block 183. When lower movable block end 1831 bypasses the arc-shaped stopper 174 and falls into the inside of the arc-shaped stopper 174, the lower movable block 183 is accommodated in the notch 1611 of the driving wheel 161, making full use of the space of the driving wheel body, optimizing the internal design of the infusion mechanism module to reduce the volume of the infusion device.

Figure 9A:
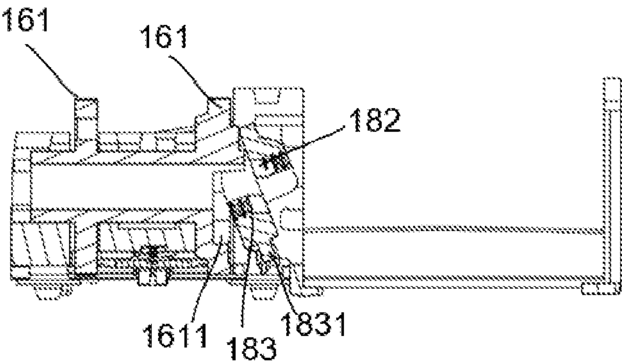
FIG. 9*a*-FIG. 9*d* are schematic views of the movable block opened or closed according to an embodiment of the present invention, respectively.
Figure 9B:
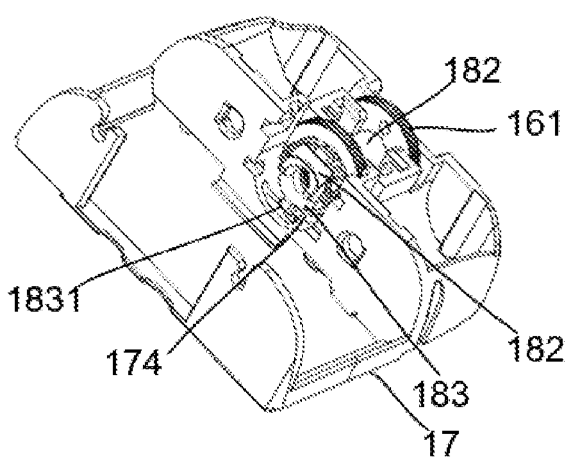
Figure 9C:
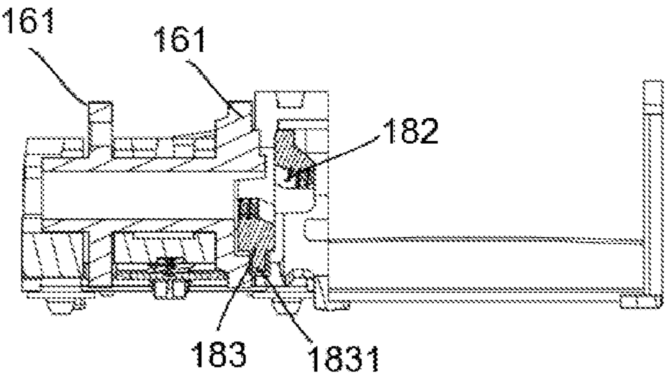
Figure 9D:
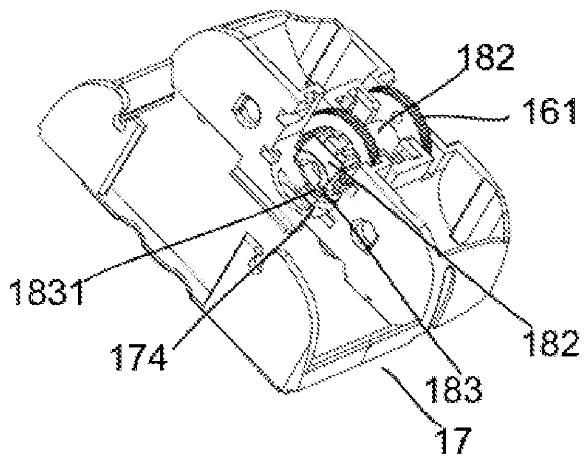

It should be noted here that "inside" and "outside" are relative to the arc-shaped blocking member 174, and belong to the concept of relative position. The positional relationship is as shown in FIG. 9*b* and FIG. 9*d*.

Figure 10A:
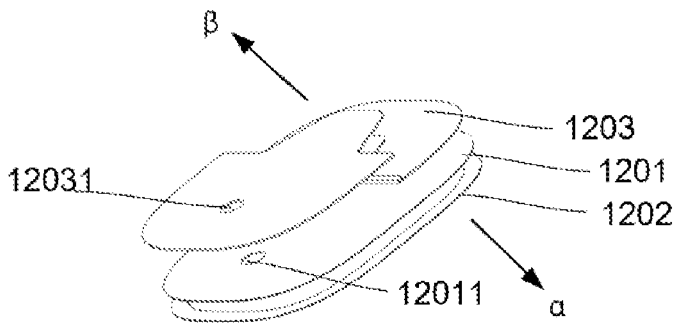
FIG. 10*a* a schematic view of the adhesive patch according to an embodiment of the present invention.
Figure 10B:
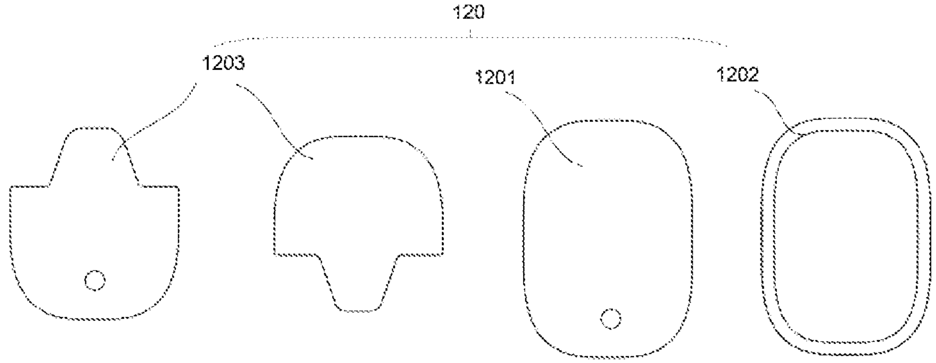
FIG. 10*b* a schematic view of each layer of the adhesive patch according to an embodiment of the present invention.
Figure 10C:
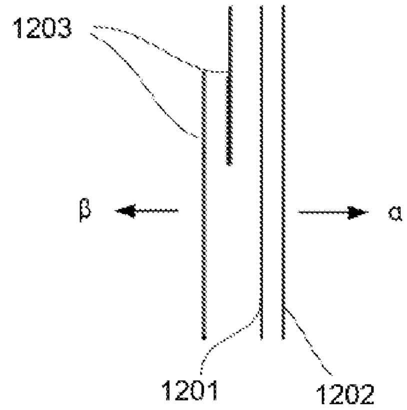
FIG. 10*c* a schematic view of the cascading sequence of the adhesive patch according to an embodiment of the present invention.

FIG. 10*a* a schematic view of the adhesive patch according to an embodiment of the present invention. FIG. 10*b* a schematic view of each layer of the adhesive patch according to an embodiment of the present invention. FIG. 10*c* is a schematic view of the cascading sequence of the adhesive patch according to an embodiment of the present invention.

Adhesive patch 120 comprises a tape 1201, the first side α of the tape 1201 is firmly connected to the infusion mechanism module 110, and the second side β is coated with paste material for pasting the infusion device to the host skin surface. The material of the tape 1201 is one of the following: polyethylene, polypropylene, non-woven or cotton. The tape 1201 is in direct contact with the skin of the host. According to the actual use environment, the above materials can avoid the adverse reactions caused by the tape 1201 contacting the skin for a long time. In order to adapt to the host skin movement, such as tortuous, stretching, etc., the thickness of the tape 1201 is extremely thin, for example, about 0.001 um~1 um. Thin tape can cause other problems, such as static electricity from the host skin, or intense skin movement can cause the edges of the tape to warp. Once the edge of the tape warps, the area of the warped edge of the tape 1201 will gradually increase with the increase of the use time, resulting in the decrease of the adhesion force between the tape 1201 and the skin, which may lead to the displacement or shedding of the infusion device, affecting the user experience.

A protective film 1202 is added on the outer edge of the first α face of the tape 1201, and the rockwell hardness of the protective film 1202 is greater than that of the tape 1201. Preferably, in the embodiment of the invention, the rockwell hardness of the protective film 1202 is 80~100 HRM.

Preferably, in the embodiment of the invention, the protective film 1202 is one of polycarbonate, polyamide, polyformaldehyde, polyphenyl ether, polyester, polyphenylene sulfide and polyaryl ester.

In a more preferred embodiment of the invention, the protective film 1202 is polyethylene terephthalate (PET), and its rockwell hardness is 90~95 HRM.

The outer edge profile of the protective film 1202 is compatible with the outer edge profile of the tape 1201. Here, the outer edge profile size, bending radius, shape and other parameters of the protective film 1202 are consistent with the outer edge profile parameters of the tape 1201, so that every part of the outer edge of the tape 1201 can be fitted with the protective film 1202.

In the preferred embodiment of the invention, the thickness of the protective film is 0.01~100 um.

In the preferred embodiment of the invention, the protective film 1202 is annular; the hollow and annular protective film 1202 can be fitted to the first side α of the tape 1201 comprehensively, and no interference with the infusion device. Secondly, the inner edge of the annular protective film is consistent with the outer edge contour, which is more beautiful and enhances the user experience.

In the embodiment of the invention, the tape 1201 is provided with a first through hole 12011, and the position of the first through hole 12011 corresponds to the infusion needle 121 of the infusion device, which is used for the infusion needle 121 to pierce the skin of the host.

The second side β of the tape 1201 is also provided with at least one layer of release paper 1203, as the release paper 1203 can prevent the adhesive material of the second side β of the tape 1201 from adhering and can protect the adhesive material from contamination of the anti-sticking paper.

In the preferred embodiment of the invention, the release paper 1203 is a single silicon release paper, and its peeling force is 30 g~50 g.

In the embodiment of the invention, the release paper 1203 is provided with a second through hole 12031, and the position of the second through hole 12031 corresponds to the first through hole 12011, so that the infusion needle 121 of the infusion device can pass through the first through hole 12011 and the second through hole 12031 to pierce the host skin.

For the convenience of users to peel off release paper 1203 and tape 1201, and save space, the release paper 1203 is preferred to be two layers, and the peel openings are relative to each other, and the peel openings of one layer are bent outwardly and covered by the peel openings of the other layer. Combined with the above, adhesive patch 120 from side α to β is protective film 1202, tape 1201 and release paper 1203 in sequence.

Figure 11A:
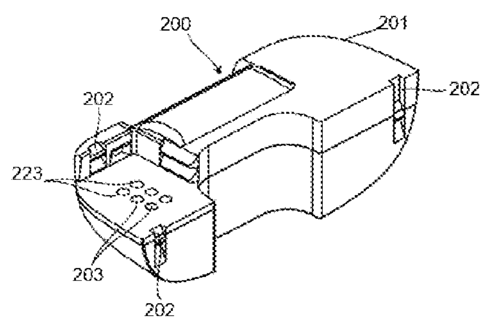
FIG. 11*a* and FIG. 11*b* are schematic views of the control mechanism module and infusion mechanism module according to another embodiment of the present invention.
Figure 11B:
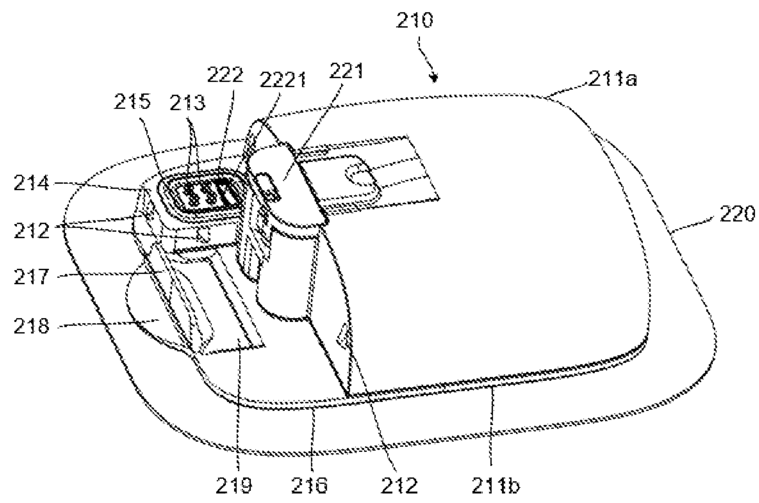

FIG. 11*a* and FIG. 11*b* are schematic views of the control mechanism module and infusion mechanism module according to another embodiment of the present invention.

In the embodiment of the present invention, the main difference with the control mechanism module 100 and the infusion mechanism module 110 (as shown in FIG. 2 and FIG. 3) is that the control mechanism module 200 includes a first electrical connection 203 and a first physical component 223, the infusion mechanism module 210 includes a second electrical connection 213 and an in-position detection module 222, which will be described in detail below. The other parts are the same as the aforementioned control mechanism module 100 and the infusion mechanism module 110, here will not be repeated.

The second electrical connection 213 and in-position detection module 222 are both arranged on the convex portion 214 of the upper case 211 of the infusion mechanism module 210, which can make the full use of the internal space of the infusion device and optimize the circuit layout of the circuit board or three-dimensional circuit set up. In other embodiments of the invention, the second electrical connection 213 and in-position detection module 222 may also be arranged at other positions of the infusion mechanism module 210, which are not limited here.

The in-position detection module 222 comprises a second physical component 2221, such as a voltage variant resistance device, a magnetic part, an inductor coil, a capacitor, etc, is understood by technical personnel in this field that the physical components mentioned above can also be combined. In addition, the physical components that can be used by the in-position detection module 222 are not limited to this, and other physical components that can trigger position signals can be used here. The first physical component 223 is electrically operable, with the second physical component 2221. The "operable" electrical connection here means that the first physical component 223 and the second physical component 2221 have different electrical connections according to the type of the first physical component 223 and the second physical component 2221.

Figure 12A:
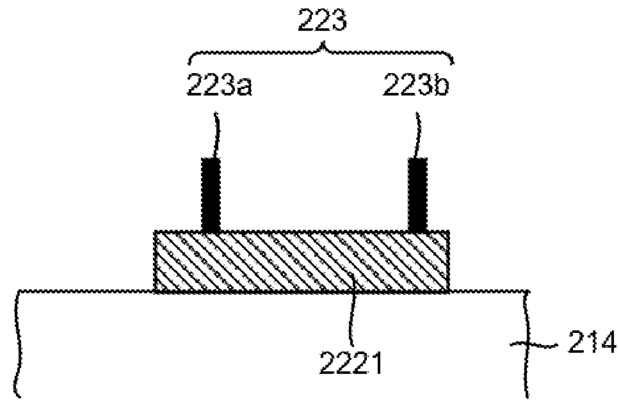
FIG. 12*a* is a schematic view of the in-position detection module comprising a voltage transformer device according to an embodiment of the invention.
Figure 12B:
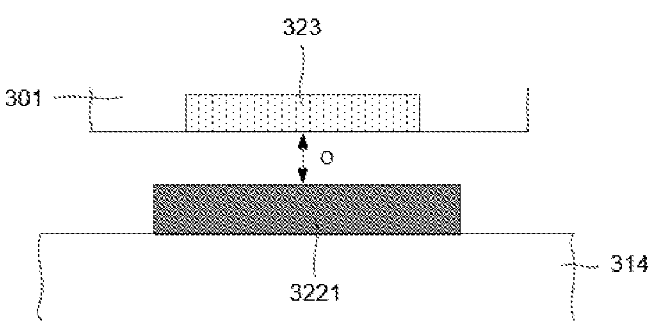
FIG. 12*b* is a schematic view of the in-position detection module comprising a magnetic component according to an embodiment of the invention.

FIG. 12*b* is a schematic view of the in-position detection module comprising a magnetic component according to an embodiment of the invention.

In the embodiment of the present invention, the second physical component 2221 of the in-position detection module is a voltage variant resistance device, which is sensitive to pressure, and the change of the external device's pressure on the voltage variant resistance device can cause the change of the resistance value of the voltage variant resistance device, which can be linear or nonlinear. This principle can be used to detect the firmness of the combination between control mechanism module 200 and infusion mechanism module 210.

The second physical component 2221 is a voltage transformer device located on the convex portion 214 of the infusion mechanism module 210, and the corresponding first physical component 223 on the control mechanism module is a rigid electrical contact point. The rigid electrical contact point contacts with the voltage transformer device when the control mechanism module is installed on the infusion mechanism module. Technicians in this field know that to form a closed-loop circuit, the number of rigid electrical contact points is two, namely the first rigid electrical contact point 223*a* and the second rigid electrical contact point 223*b*.

In the embodiment of the invention, when the control mechanism module and the infusion mechanism module are normally connected, the rigid electrical contact point contacts with the voltage variant resistance device to generate a base pressure F1, and corresponding to the base pressure, the voltage variant resistance device generates a base resistance R1. When the connection between the control mechanism module and the infusion mechanism module becomes loose and lost its position, the pressure generated by contact between the rigid electrical contact point and the voltage variant resistance device decreases, for example to F2, apparently F2<F1, corresponding pressure variable resistance device resistance R2, if the voltage variant resistance device is a positive feedback device, the R2<R1, on the contrary, if the voltage variant resistance device is a negative feedback device, the R2>R1. When the connection between the control mechanism module and the infusion mechanism module becomes tight, the pressure generated by contact between the rigid electrical contact point and the varistor device is increased, for example, change to F3, obviously the F3>F1, correspondingly, the resistance of the pressure variable resistance device changes to R3, if the voltage variant resistance device is a positive feedback device, the R3>R1, on the contrary, if the voltage variant resistance device is a negative feedback device, the R3<R1.

Whether the voltage transformer device is a positive feedback device or a negative feedback device, there is a unique correspondence between the resistance value and the pressure, and the pressure is positively correlated with the firmness of the combination between the control mechanism module and the infusion mechanism module, so the resistance value of the voltage variant resistance device indirectly represents the firmness of the combination between the control mechanism module and the infusion mechanism module.

In the preferred embodiment of the invention, the resistance value R of the voltage variant resistance device is converted into the relative position data between the control mechanism module and the infusion mechanism module after being calculated by the relevant algorithm, and then transmitted wirelessly by the control mechanism module to a remote device, such as PDM (Personal Diabetes Manager), mobile terminal, etc., it is convenient for users to know the tightness of the installation of the control mechanism module in real-time.

In the preferred embodiment of the invention, the voltage variant resistance device is a voltage variable resistance conductive rubber strip. The voltage variable resistance conductive rubber strip is easy to cut and can be processed into any shape to meet the testing device's structural design requirements.

FIG. 12*b* is a schematic view of the in-position detection module comprising a magnetic component according to an embodiment of the invention.

In the embodiment of the invention, the second physical component 4231 of the in-position detection module is a magnetic component, which provides a stable magnetic field. At different effective distances, magnetic components have different magnetic field directions and magnetic field strengths. This principle can be used to detect the firmness of the combination between the control mechanism module and the infusion mechanism module.

The second physical component 4231 is the magnetic component, and the corresponding first physical component 222 on the control mechanism module is the magnetic sensor. When the control mechanism module is mounted on the infusion mechanism module, the magnetic sensor inducts either the magnetic field direction or the magnetic field strength of the magnetic component, or both. The direction or strength of the induced magnetic field varies with the distance O between the magnetic sensor and the magnetic component. Preferably, the magnetic field strength H of the magnetic component is induced by the magnetic sensor.

In the embodiment of the invention, when the control mechanism module is normally connected to the infusion mechanism module, the distance between the magnetic sensor and the magnetic component is O1, and the magnetic sensor senses the basic magnetic field strength H1 of the magnetic component. When the connection between the control mechanism module and the infusion mechanism module becomes loose and loses position, the distance between the magnetic sensor and the magnetic component becomes larger, for example, O2, O2>O1, and the magnetic field strength of the magnetic component induced by the corresponding magnetic sensor becomes H2, obviously H2<H1. When the connection between the control mechanism module and the infusion mechanism module becomes tight, the distance between the magnetic sensor and the magnetic component becomes smaller, for example, O3, there O3<O1, and the magnetic field strength of the magnetic component that the corresponding magnetic sensor becomes H3, obviously H3>H1.

No matter how the distance O between the magnetic sensor and the magnetic component changes, there is a unique correspondence between the distance O and the magnetic field strength H, and the distance between the magnetic sensor and the magnetic component is related to the firmness of the control mechanism module and the infusion mechanism module, so the magnetic field strength H of the magnetic component induced by the magnetic sensor indirectly represents the firmness of the combination of the control mechanism module and the infusion mechanism module.

In the preferred embodiment of the invention, the magnetic field strength H of the magnetic component induced by the magnetic sensor is converted into the relative position data between the control mechanism module and the infusion mechanism module after the relevant algorithm operation, and then transmitted wirelessly to the remote device, such as PDM (Personal Diabetes Manager), mobile terminal, etc., by the control mechanism module 200. It is convenient for users to know the tightness of installing the control mechanism module in real-time.

Figure 12C:
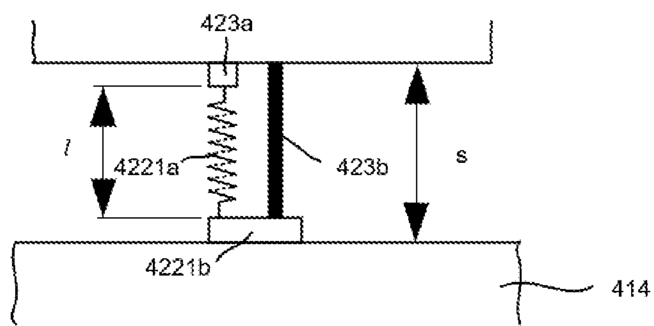
FIG. 12*c* is a schematic view of the in-position detection module comprising an inductor coil according to an embodiment of the invention.

FIG. 12*c* is a schematic view of the in-position detection module comprising an inductor coil according to an embodiment of the invention.

In the embodiment of the invention, the second physical component 5231 of the in-position detection module is an inductor coil, and the following formula can calculate the inductance value L of the inductor coil:

$$L = \frac{0.01 * D * N^2}{\frac{l}{D} + 0.44}$$

In the formula,

D is the diameter of the inductor coil;

l is the length of the inductor coil;

N is the number of turns of the inductor coil.

For the same inductor coil, its diameter D and the number of turns N will not change, and the length l can vary depending on the extrusion force or the tensile force at both ends; when the length l changes, its inductance value L will also change. This principle can be used to detect the firmness of the combination between the control mechanism module and the infusion mechanism module.

The second physical component comprises an inductor coil 4221*a* and a conductive boss 4221*b*. The conductive boss 4221*b* is located on the convex portion 414, and the inductor coil 4221*a* is electrically connected with the conductive boss 4221*b*. Correspondingly, the first physical component on the control mechanism module comprises a pressing part 423 *a* in contact with one end of the inductor coil and an elastic electrical contact point 423 *b* electrically connected with the other end of the inductor coil through conductive boss 4221*b*. What technicians in this field can know is that in order to obtain the inductance value L of the inductor coil, the conductive boss 4221*b*, the pressing part 423 *a* and the elastic electrical contact point 423 *b* are all conductive materials.

In the embodiment of the invention, when the control mechanism module is normally connected to the infusion mechanism module, the pressing part 423*a* contacts with one end of the inductor coil, and the elastic electrical contact point 423*b* contacts with the other end of the inductor coil. The pressing part 423*a*, the inductor coil and the elastic electrical contact point 423*b* form a closed circuit, and the internal circuit in the control mechanism module can obtain the inductance value L of the inductor coil. At this time, the distance between the control mechanism module and the infusion mechanism module is s1, the length of the inductor coil is l1, corresponding to the length of the inductor coil, the basic inductance value of the inductor coil is l1. When the connection between the control mechanism module and the infusion mechanism module becomes loose and loses position, the distance between the control mechanism module and the infusion mechanism module becomes s2, the pressing part 423*a* moves with the control mechanism module, the length of the inductor coil becomes l2, s2>s1, l2>l1, and the inductance value of the inductor coil becomes L2, obviously L2<L1. When the connection between the control mechanism module and the infusion mechanism module becomes tight, the distance between the control mechanism module and the infusion mechanism module becomes s3, and the pressing part 423*a* moves with the control mechanism module, the length of the inductor coil becomes l3, s3<s1, l3>l1. At this time, the inductance value of the inductor coil becomes L3, obviously L3>L1. Regardless of the distance between the control mechanism module and the infusion mechanism module, the elastic electrical contact 423*b* can maintain good electrical contact with the inductor coil because of its elastic property unless the control mechanism module is completely removed from the infusion mechanism module.

No matter how the length l of the inductor coil changes, there is a unique correspondence between the length l and the inductor value L, while the length l of the inductor coil is related to the firmness of the combination between the control mechanism module and the infusion mechanism module. Therefore, the inductance value L of the inductor coil indirectly represents the firmness of the combination between the control mechanism module and the infusion mechanism module.

In the preferred embodiment of the invention, the inductance value L of the inductor coil is converted into the relative position data between the control mechanism module and the infusion mechanism module after being calculated by the relevant algorithm, and then transmitted wirelessly to a remote device, such as PDM (Personal Diabetes Manager), mobile terminal, etc. It is convenient for users to know the tightness of installing the control mechanism module in real-time.

Figure 12D:
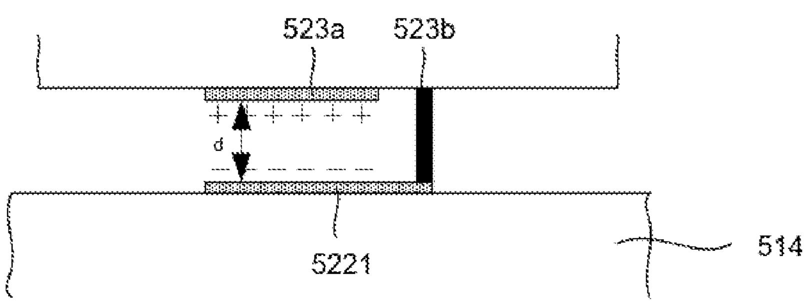
FIG. 12*d* is a schematic view of the in-position detection module comprising a capacitive lower plate according to an embodiment of the invention.

FIG. 12*d* is a schematic view of the in-position detection module comprising a capacitive lower plate according to an embodiment of the invention.

In the embodiment of the invention, the second physical component 5221 of the in-position detection module comprises a lower electrode plate of the capacitor, and the first physical component 523 comprises an upper electrode plate 523*a* of the capacitor and an elastic electrical contact 523*b*. The combination between the upper electrode plate 523*a* and the lower electrode plate is a complete capacitor, and the elastic electrical contact 523*b* is used to make electrical contact with the lower electrode plate to form a closed circuit. An internal circuit in the control mechanism module can measure the capacitance value C of the capacitor. The following formula can determine the capacitance value C:

$$C = \frac{\varepsilon * S}{4\pi kd}$$

In the formula,

ϵ is a constant;

S is the frontal area of the capacitor's upper and lower plates;

K is the electrostatic force constant;

D is the distance between the upper and lower plates of the capacitor.

For the capacitance composed of the upper and lower plates, the positive area S and the static power constant ϵ are fixed, and the distance d between the upper and lower plates can change with the firmness of the combination between the control mechanism module and the infusion mechanism module. When the distance D changes, the capacitance C will also change. This principle can be used to detect the firmness of the combination between the control mechanism module and the infusion mechanism module.

As mentioned above, the first physical component 523 comprises a capacitive upper plate 523$a$ and an elastic electrical contact 523$b$. The combination between the upper plate 523$a$ and the lower plate is a complete capacitor, and the elastic electrical contact 523$b$ is used to make electrical contact with the lower plate to form a closed circuit. Technicians in this field can know that elastic electrical contact 523$b$ is a conductive material in order to obtain a capacitance value.

In the embodiment of the invention, the control mechanism module and the infusion mechanism module are normally connected, the upper plate 523$a$ and the lower plate form a capacitor, elastic electrical contact 523$b$ is in contact with the lower plate and is used to provide the lower plate with a charge opposite to the upper plate 523$a$, the distance between the upper plate 523$a$ and the lower plate is d1, corresponding to the upper and lower plate distance, the capacitance of the capacitor is C1. When the connection between the control mechanism module and the infusion mechanism module becomes loose and loses position, the distance between the control mechanism module and the infusion mechanism module becomes d2, $d2>d1$, and the capacitance value of the capacitor becomes C2, obviously $C2<C1$. When the connection between the control mechanism module and the infusion mechanism module becomes tight, the distance between the control mechanism module and the infusion mechanism module becomes d3, $d3<d1$, and then the capacitance value of the capacitor becomes C3, obviously $C3>C1$. Regardless of the distance between the control mechanism module and the infusion mechanism module, elastic electrical contact 523$b$ can maintain good electrical contact with the inductor coil because of its elastic property unless the control mechanism module is completely removed from the infusion mechanism module.

No matter how the distance d between the upper and lower plates of the capacitor changes, there is a unique corresponding relationship between the distance d and the capacitance value C, while the distance d between the upper and lower plates is related to the firmness of the combination between the control mechanism module and the infusion mechanism module. Therefore, the capacitance value C of the capacitor indirectly represents the firmness of the combination between the control mechanism module and the infusion mechanism module.

In the preferred embodiment of the invention, the capacitance value of the capacitor is converted into the relative position data of the control mechanism module and the infusion mechanism module after the relevant algorithm operation and then transmitted wirelessly to the remote device, such as PDM (Personal Diabetes Manager), mobile terminal, etc., so that the user can understand the installation tightness of the control mechanism module in real-time.

Figure 13:
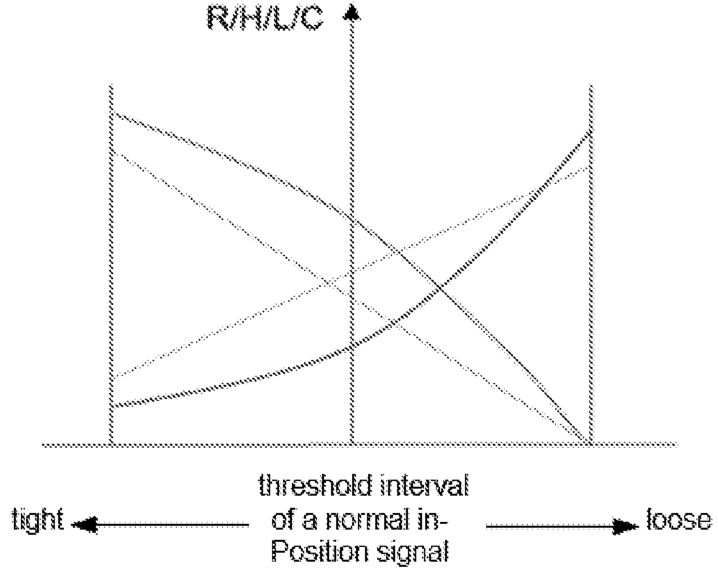
FIG. 13 is a schematic view of the threshold interval of a normal in-position signal according to an embodiment of the invention.

In the embodiment, the internal circuit is also provided with a signal threshold interval of the control mechanism module normally in position. FIG. 13 is a schematic view of the threshold interval of a normal in-position signal according to an embodiment of the invention. The in-position detection module may be one or more combinations of voltage transformer devices, inductor coils, magnetic components or capacitors. The parameter signals and the bonding degree of the control mechanism module and the infusion mechanism module may be linear or nonlinear, and may be positive feedback or negative feedback. Whatever the relationship, the parameter signal is uniquely corresponding to the firmness of the bond between the control mechanism module and the infusion mechanism module, and thus the parameter signal has a unique maximum threshold and a unique minimum threshold, the interval between the above maximum threshold and minimum threshold is the normal in-place threshold interval, during which the control mechanism module is properly fixed to the infusion mechanism module.

If the parameter signal exceeds the normal in-position threshold range, it indicates that the control mechanism module is loose, or the control mechanism module is too tightly combined with the infusion mechanism module due to external extrusion. At this time, the internal circuit sends out an alarm signal, prompting the user to press the control mechanism module, or replace the control mechanism module, or cancel the external pressure.

In order to meet the needs of different users, the expression form of an alarm signal can be designed as one or more combinations of luminous signal, vibration signal and sound signal.

FIG. 14 is a schematic view of the internal mechanism module of the infusion mechanism module comprising a blockage detection module according to another embodiment of the present invention.

In the embodiment of the present invention, the infusion device is also provided with a blockage detection module, which is operably connected to the control mechanism module, and is used to sense and measure related physical parameters during the drug filling process or the drug infusion process to confirm whether a blockage has occurred. The blockage detection module includes a detection circuit (not shown) and at least one detection element 311. The detection circuit is arranged in the control mechanism module, and the detection element 311 is arranged in the infusion mechanism module 310. The detection circuit cooperates with at least one detection element 311 to provide corresponding signals, data or information that need to be analyzed and processed for the purpose of blockage detection. The detection circuit also stores preset thresholds for various related physical parameters, and includes a comparator that compares the sensed related physical parameters with the preset thresholds. When the sensed related physical parameters are greater than or less than the corresponding preset thresholds, the detection circuit sends out an alarm signal to remind the user that the blockage occurs, stop the infusion, replace the infusion mechanism module, or perform other operations to avoid potential safety hazards.

In an embodiment of the present invention, the detection element 311 is a component of the infusion device itself, the power unit 313, preferably, the power unit 313 is an electric driven linear drive or electric heating driven linear drive, such as a shape memory alloy. A timer is set in the detection circuit to record the time it takes for the power unit 313 to pull the drive end 314 to push the drive wheel 315 to rotate and then to push the piston 312 forward by one step. When the time for the piston 312 moving forward by one step is greater than a certain preset, the detection circuit sends out an alarm signal to remind the user that a blockage occurs. In the embodiment of the present invention, the power unit is a component of the infusion device itself. Using this component as a detection element can optimize the internal arrangement of the infusion device and reduce the cost.

In other inventive embodiments of the present invention, the detection element 311 is a component of the non-infusion device itself, such as one or a combination of a force sensor, an acceleration sensor, and a position detection element. As shown in FIG. 14, the detection element 311 is provided in the piston 312. In other embodiments of the present invention, the detection element 311 may also be provided in other parts of the infusion mechanism module 310, such as one or more places in the screw 316, or the connection point of the screw 316 and the piston 312 etc., which are not limited here. It can be flexibly set according to the actual arrangement to optimize the internal design of the infusion mechanism module.

In another embodiment of the present invention, the detection element 311 is a force sensor, preferably, the force sensor is a tension sensor. During the drug filling or infusion process, the tension sensor is used to sense the force of the power unit 313 acting on the screw 316 or the piston 312, when the sensed force is greater than a certain preset threshold, the detection circuit sends out an alarm signal to remind the user that a blockage occurs.

In one embodiment of the present invention, the detection element 311 is a force sensor, preferably, the force sensor is a pressure sensor. During the drug filling or infusion process, the pressure sensor senses the pressure applied by the piston to the drug. When the sensed pressure exceeds a certain preset threshold, the detection circuit sends out an alarm signal to remind the user that a blockage occurs.

In another embodiment of the present invention, the detection element 311 is an acceleration sensor. During the drug filling or infusion process, the acceleration sensor can sense the speed or acceleration of the screw 316 or the piston 312 moving in the reservoir 313. The detection circuit converts it into the change value of speed or acceleration per unit time. When the detected change value is less than a certain preset threshold, the detection circuit sends an alarm signal to remind the user that the blockage occurs.

In another embodiment of the present invention, the detection element 311 is a position detection element. During the drug filling or infusion process, the position detection element detects the position changes of the end of the piston 312 or the screw 316 in the reservoir 317 along the axial direction (the moving direction of the screw 316), the detection circuit converts the axial position information of the piston 312 or the end of the screw 316 into the speed or acceleration of the piston 312 or the end of the screw 316 moving in the reservoir 317 in a unit time and further calculates the change value of the speed or acceleration of the piston 312 or the end of screw 316. When the change value is less than a certain preset threshold, the detection circuit sends an alarm signal to remind the user that the blockage occurs.

Preferably, in the embodiment of the present invention, the position detection element detects the position of the end of the piston 312 or the screw 316 by a non-contact detection method. The position detection element is a magnetic element for providing a magnetic field. The detection circuit is provided with a magnetic sensor. The magnetic field intensity of the magnetic element induced will be changed with the change of the position of the magnetic element, that is, the end of the piston 312 or the screw 316. Therefore, the detection circuit can calculate the position change of the piston 312 end or the screw 316 through the change of the induced magnetic field. As described above, the blockage can be detected by the further calculation of the detection circuit. In other embodiments of the present invention, the position detection element can also detect the position of the end of the piston 312 or the screw 316 by other non-contact or contact detection methods, which is not specifically limited herein.

Preferably, in the embodiment of the present invention, the detection element 311 is provided in the piston 312, and the piston 312 is provided with at least one recess 3121 for accommodating the detection element 311. The recess 3121 is also provided with a plurality of projects 3122, for fixing the detection element 311. A positioning portion 3123 is further provided in the middle of the recess 3121 to fix the detection element 311 further, and prevent deviation of the sensing information of the detection element 311 from shaking, affecting the detection result.

In another embodiment of the present invention, the detection element 311 is a combination of a force sensor, a pressure sensor, an acceleration sensor, a position detection element, and a power unit, which can realize more accurate blockage detection and improve user experience.

In order to meet the needs of different users, the form of the alarm signal can be designed as one or more combinations of luminous signal, vibration signal, and sound signal. Different forms of signal expression are convenient for users to obtain the alarm signal in time according to their needs and take corresponding measures to enhance user experience.

Figure 15A:
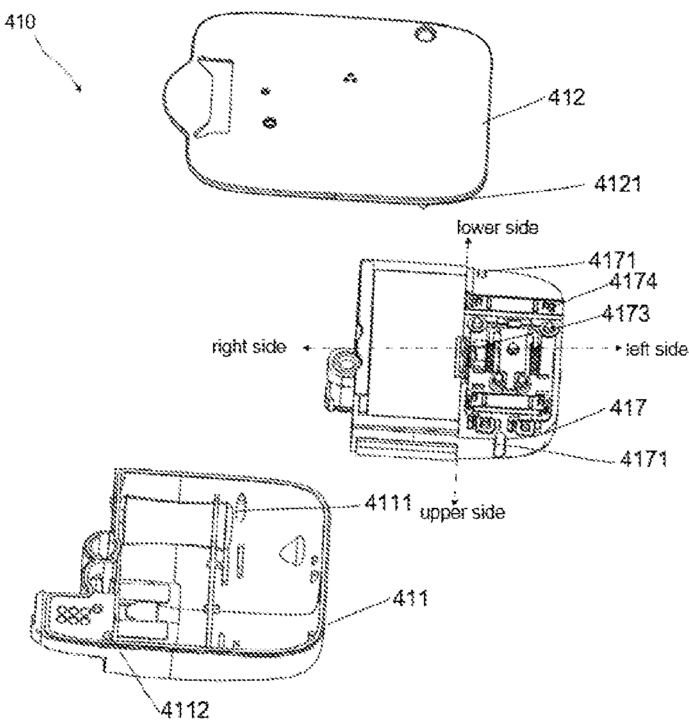
FIG. 15*a* is an exploded view of the infusion mechanism module according to an embodiment of the present invention.
Figure 15B:
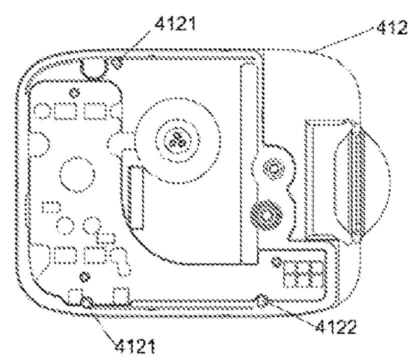
FIG. 15*b* is a schematic view of the lower case according to an embodiment of the present invention.
Figure 15C:
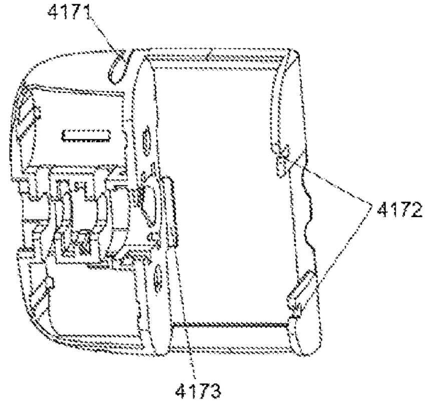
FIG. 15*c* is a schematic view of the frame according to an embodiment of the present invention.

FIG. 15*a* is an exploded view of the infusion mechanism module according to an embodiment of the present invention. FIG. 15*b* is a schematic view of the lower case according to an embodiment of the present invention. FIG. 15*c* is a schematic view of the frame according to an embodiment of the present invention.

The infusion mechanism module 410 includes an upper case 411, a lower case 412, and a frame 417 disposed between the upper case 411 and the lower case 412. The upper case 411 is provided with at least an upper case first engaging portion 4111 and an upper case second engaging portion 4112, and the lower case 412 is provided with at least a lower case first engaging portion 4121 and a lower case second engaging portion 4122. The frame 417 is provided with at least a frame first engaging portion 4171 to engage with an upper case first engaging portion 4111 and the lower case first engaging portion 4121 at the same position, improving longitudinal engaging stability of the frame 417 and the upper case 411 and the lower case 412, and reducing the complexity of the engagement. The upper case second engaging portion 4112 and the lower case second engaging portion 412 are engaged on the side of the frame 417. After the engagement, the frame 417 can be prevented from moving laterally, improving lateral engaging stability of the frame 417 and the upper case 411 and the lower case 412. Here, 'longitudinal' refers to the thickness direction of the infusion device, and 'lateral' refers to the length direction of the infusion device, as shown in FIG. 3*a*. Each engaging portion includes one or more hooks, blocks, holes, and grooves that can be engaged with each other. The position can be flexibly designed according to the shape or arrangement of the upper case 411, the lower case 412 and the frame 417, and there is no specific limitation here, as long as the longitudinal and lateral engagement stability of the upper case 411, the lower case 412 and the frame 417 can be achieved.

The lower case 412 is provided with a circuit board for supplying power to specific units, and the circuit board is a rigid circuit board or a flexible circuit board. Preferably, in the embodiment of the present invention, the circuit board is flexible. The shape of the flexible circuit board is adjustable and can be flexibly designed according to the internal space of the infusion mechanism module 410. At the same time, multiple connection ends can be provided on the flexible circuit board to be electrically connected to each electrical connection terminal on the frame 417 to optimize the circuit layout, thereby realizing the circuit conduction inside the infusion mechanism module 410 and improving the electrical connection stability of all parts.

The frame 417 is used to carry the internal parts of the infusion mechanism module 410. Here, the side of the frame 417 facing the upper case 411 is the upper side, and the side facing the lower case 412 is the lower side. Take the open end of the reservoir as the baseline, one side for accommodating the reservoir is the right side, and the other side is the left side. What needs to be explained here is that "upper side", "lower side", "left side", and "right side" are relative position concepts, and the positional relationship is shown in FIG. 15*a*. The right side of the frame 417 is provided with a reservoir accommodating cavity for accommodating the reservoir, the shape is adapted to the reservoir, and the lower side of the frame 417 is provided with a plurality of lugs 4173 for carrying the reservoir. The right side of the frame 417 is also provided with a plurality of second frame engaging portions 4172, and a plurality of reservoir engaging portions (not shown) are provided on the outer side of the reservoir to engage with the frame second engaging portion 4172, so that the reservoir and the frame 417 can connect stably.

A driving wheel assembly and a power supply are arranged on the left side of the upper side of the frame 417, and the power supply is a double-row battery, which is arranged on both sides of the driving wheel assembly, respectively. The electrical connection elements in the infusion mechanism module 410 are all arranged on the left side of the lower side of the frame 417, and the power supply supplies power to the components, which is connected to the circuit board through the approximately "L"-shaped elastic conductor to realize the circuit conduction inside the infusion mechanism module 410. As shown in FIG. 4*a* and FIG. 4*c*, the frame 417 is provided with a plurality of positioning posts 138 of the elastic conductor 136, the position is adapted to the position of the power supply, and is used to fix the elastic conductor 136; the frame 417 is also provided with holes 4174 (as shown in FIG. 15*a*), the elastic conductor 136 realizes the electrical connection between the power supply and the circuit board, which are provided on the upper and lower sides of frame 137, respectively, through the holes 4174, thereby realizing power supply to all electrical components. A rotating shaft 1315 is also provided on the frame 417, for sleeving the driving unit 1310 and providing a fulcrum for the rotation of the driving unit 1310, and is arranged between the driving wheels 134. A conductive retaining wall 1318 is also provided on the end of the driving unit 1310, for limiting the driving end of the driving unit 1310. A conductive tower-spring 1315 is also provided on the drive unit 1310, which is used to connect the drive unit 1310 and the circuit board. The conductive tower-spring 1315 has a large diameter in the middle part and a small diameter in the end parts, which can fix the drive unit 1310 and improve the electrical connection stability with the circuit board. A plurality of positioning tables 1319 of power unit 1311 are also arranged between the conductive platform 1314 and the elastic conductor 1316, so that the power unit 1311 can only be arranged along the linear position defined between the positioning platforms 1319, and prevent the power unit 1311 from being touched with other conductive elements, which will cause a short circuit and fail the infusion device. A conductive platform positioning post 1317 and a stop 1316 is also provided at the end of the frame to fix the conductive platform 134, as shown in FIG. 7. The specific features of each component are as described above and will not be repeated here. Through the above arrangement of the frame 417, the components of the infusion mechanism module 410 can be integrated into the frame 417, making full use of the internal space of the infusion mechanism module 410, improving the integration of the internal arrangement, and effectively reducing the volume of the infusion mechanism module 410. At the same time, the physical connection stability and electrical connection stability of each component can be ensured, and the electrical connection reliability of the internal arrangement of the infusion mechanism 410 can be improved.

In the embodiment of the present invention, the frame 417 may be a molded member including upper side, lower side, left side and right side or integrated by splicing all or some components. For example, part of the components are a molded member and then integrated by splicing with other components, or integrated by splicing each component. Each component itself can also be a molded member or integrated by splicing according to actual needs, and there is no specific limitation here. When the frame is a molded member, the process is simple, the volume is small, the connection is firm, the material is saved, and the cost is reduced. When the frame is integrated by splicing, it can be flexibly selected according to the requirements of the components that the frame needs to carry to optimize the internal design of the infusion mechanism module.

As a summary, the present invention discloses a skin patch drug infusion device. The infusion mechanism module is provided with a conductive tower-spring, including a middle part with a small diameter and two end parts with a large diameter in the axial direction, for fixing the driving unit, which can prevent the driving unit from rotating due to accidental touch and affect the accuracy of infusion. At the same time, the conductive tower-spring is electrically connected the driving unit with the specific connection end on the circuit board or three-dimensional circuit, when the conductive tower-spring is compressed, the two ends of the conductive tower-spring are provided with multiple turns of springs to contact with the driving unit and the specific connection end on the circuit board or the three-dimensional circuit, respectively, which can enhance the electrical connection between the conductive tower-spring and the driving unit and the specific connection end on the circuit board or three-dimensional circuit, improving the reliability of the electrical connection.

While the invention has been described in detail regarding the specific embodiments of the present invention, it should be understood that it will be appreciated by those skilled in the art that the above embodiments may be modified without departing from the scope and spirit of the invention. The appended claims define the scope of the invention.

The invention claimed is:

1. A skin patch drug infusion device, comprising:

an infusion mechanism module, wherein the infusion mechanism module includes a circuit module, the circuit module includes:

a circuit board or a three-dimensional circuit;

a driving unit, for pushing a driving wheel of the infusion mechanism module to implement drug infusion;

a conductive tower-spring, including a middle part with a small diameter and two end parts with large diameters in an axial direction, for fixing the driving unit and electrically connecting the driving unit and a connection end on the circuit board or the three-dimensional circuit;

a control mechanism module, electrically connected with the infusion mechanism module; and an adhesive patch, for attaching the infusion mechanism module and the control mechanism module to a skin surface, wherein the infusion mechanism module further includes a frame, the frame is provided with a rotation shaft, the driving unit is sleeved on the rotation shaft and rotated around the rotation shaft, the diameter of the middle part of the conductive tower-spring remains the same, the diameters of the two end parts gradually expand in a horn-like shape, and the middle part of the conductive tower-spring is interference fit with the rotating shaft.

2. The skin patch drug infusion device of claim 1, wherein the two end parts of the conductive tower-spring are symmetrical.

3. The skin patch drug infusion device of claim 2, wherein when the conductive tower-spring is compressed, the two end parts of the conductive tower-spring are provided with multiple turns of springs to contact with the driving unit and the connection end on the circuit board or the three-dimensional circuit, respectively.

4. The skin patch drug infusion device of any claim 1, wherein the driving unit includes at least one driving end, and a number of the at least one driving end is one or two.

5. The skin patch drug infusion device of claim 1, wherein the circuit board is flexible.

6. The skin patch drug infusion device of claim 1, wherein the infusion mechanism module further includes a power supply and an elastic conductor with protrusions, used for electrically connecting the power supply and the connection end on the circuit board or the three-dimensional circuit.

7. The skin patch drug infusion device of claim 6, wherein the elastic conductor is at least one of a conductive spring, a conductive leaf spring, a conductive rubber and a conductive silica gel.

8. The skin patch drug infusion device of claim 6, wherein the power supply is a double-row battery pack.

9. The skin patch drug infusion device of claim 1, wherein the infusion mechanism module and the control mechanism module are detachable to each other, and the control mechanism module is reusable.

10. The skin patch drug infusion device of claim 1, wherein the infusion mechanism module and the control mechanism module are disposed in one housing, discarded together after a single-use.

11. The skin patch drug infusion device of claim 1, wherein the control mechanism module is provided with a plurality of first electrical contacts exposed on a surface of the control mechanism module and the infusion mechanism module is provided with a plurality of second electrical contacts electrically connected with the first electrical contacts.

12. The skin patch drug infusion device of claim 11, wherein the first electrical contacts are rigid metal pins or elastic conductive members, or the second electrical contacts are rigid metal pins or elastic conductive members.

13. The skin patch drug infusion device of claim 1, wherein the infusion mechanism module further includes a case, the case is provided with an outward extending portion, and a block is provided on an outside of the outward extending portion.

14. The skin patch drug infusion device of claim 1, wherein the adhesive patch comprises a tape and a protective film, a first side of the tape is fixedly connected with the skin patch drug infusion device, and a second side opposite the first side of the tape is coated with a paste material, the protective film is fixed around an outer edge of the first side of the tape, an outer edge of the protective film contour corresponds to the outer edge of the first side of the tape, and a rockwell hardness of the protective film is higher than a rockwell hardness of the tape.

* * * * *